United States Patent
Bake et al.

(10) Patent No.: US 10,966,733 B2
(45) Date of Patent: Apr. 6, 2021

(54) IMPLANT SPECIFIC DRILL BIT IN SURGICAL KIT FOR CARTILAGE REPAIR

(71) Applicant: EPISURF IP-MANAGEMENT AB, Stockholm (SE)

(72) Inventors: Nina Bake, Lidingö (SE); Karin Wermelin, Bromma (SE); Manuel Otero Quevedo, Stockholm (SE); Niklas Hero, Bankeryd (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 0 days.

(21) Appl. No.: 16/802,865

(22) Filed: Feb. 27, 2020

(65) Prior Publication Data

US 2020/0187961 A1    Jun. 18, 2020

Related U.S. Application Data

(63) Continuation of application No. 15/018,812, filed on Feb. 8, 2016, now Pat. No. 10,603,049, which is a
(Continued)

(30) Foreign Application Priority Data

Sep. 2, 2011    (EP) .................................. 11179923

(51) Int. Cl.
*A61B 17/16* (2006.01)
*A61B 17/17* (2006.01)
(Continued)

(52) U.S. Cl.
CPC ...... *A61B 17/1615* (2013.01); *A61B 17/1604* (2013.01); *A61B 17/1635* (2013.01);
(Continued)

(58) Field of Classification Search
None
See application file for complete search history.

(56) References Cited

U.S. PATENT DOCUMENTS

| 4,180,910 A | 1/1980 | Straumann et al. |
| 4,197,645 A | 4/1980 | Scheicher |

(Continued)

FOREIGN PATENT DOCUMENTS

| CN | 102083374 A | 6/2011 |
| EP | 1 698 307 A1 | 9/2006 |

(Continued)

OTHER PUBLICATIONS

Extended European Search Report dated Dec. 17, 2018 in European Patent Application No. 18189755.4.
(Continued)

*Primary Examiner* — Khaja Ahmad
(74) *Attorney, Agent, or Firm* — Faegre Drinker Biddle & Reath LLP

(57) ABSTRACT

A drill tool for implant surgery including a first drill part having a first, smaller diameter for drilling a recess for an implant post and a second drill part having a second, larger diameter for drilling a recess for an implant hat is disclosed. The second drill part has one or more shape cutting edges and one or more sharp pre-cutting edges extending beyond said one or more shape cutting edges.

14 Claims, 26 Drawing Sheets

Related U.S. Application Data continuation-in-part of application No. 14/342,302, filed as application No. PCT/EP2012/067024 on Aug. 31, 2012, now Pat. No. 9,254,196.

(60) Provisional application No. 61/530,497, filed on Sep. 2, 2011.

(51) Int. Cl.
    *A61F 2/46*           (2006.01)
    *A61F 2/30*           (2006.01)
    *A61B 90/00*          (2016.01)
    *A61B 34/10*          (2016.01)

(52) U.S. Cl.
CPC .......... *A61B 17/17* (2013.01); *A61F 2/30756* (2013.01); *A61F 2/4618* (2013.01); *A61F 2/4684* (2013.01); *A61B 17/1764* (2013.01); *A61B 2034/108* (2016.02); *A61B 2090/034* (2016.02); *A61F 2002/30759* (2013.01); *A61F 2002/30948* (2013.01); *A61F 2002/4662* (2013.01); *A61F 2002/4687* (2013.01)

(56) References Cited

U.S. PATENT DOCUMENTS

| | | | |
|---|---|---|---|
| 4,964,865 A | 10/1990 | Burkhead et al. | |
| 5,520,692 A | 5/1996 | Ferrante | |
| 5,658,305 A | 8/1997 | Baker | |
| 5,716,360 A | 2/1998 | Baldwin et al. | |
| 5,743,916 A | 4/1998 | Greenberg et al. | |
| 5,976,147 A | 11/1999 | LaSalle et al. | |
| 6,063,091 A | 5/2000 | Lombardo et al. | |
| 6,165,177 A | 12/2000 | Wilson et al. | |
| 6,251,143 B1 | 6/2001 | Schwartz et al. | |
| 6,306,142 B1 | 10/2001 | Johanson et al. | |
| 6,520,964 B2 | 2/2003 | Tallarida et al. | |
| 6,799,066 B2 | 9/2004 | Steines et al. | |
| 7,658,879 B2 | 2/2010 | Solar | |
| 7,713,305 B2 | 5/2010 | Ek | |
| 7,824,181 B2 | 11/2010 | Sers | |
| 7,867,234 B2 | 1/2011 | Collazo | |
| 7,981,122 B2 | 7/2011 | Labadie et al. | |
| 8,062,302 B2 | 11/2011 | Lang et al. | |
| 8,066,708 B2 | 11/2011 | Lang et al. | |
| 8,083,745 B2 | 12/2011 | Lang et al. | |
| 8,105,330 B2 | 1/2012 | Fitz et al. | |
| 8,460,304 B2 | 6/2013 | Fitz et al. | |
| 8,641,721 B2 | 2/2014 | Aram et al. | |
| 8,882,818 B1 | 11/2014 | Vestgaarden | |
| 8,945,135 B2 | 2/2015 | Ries et al. | |
| 9,009,012 B2 | 4/2015 | Bake et al. | |
| 9,216,089 B2 | 12/2015 | Major et al. | |
| 9,254,196 B2 | 2/2016 | Bake et al. | |
| 9,386,999 B2 | 7/2016 | Robertson et al. | |
| 9,826,993 B2 | 11/2017 | Bake et al. | |
| 2002/0049448 A1 | 4/2002 | Sand et al. | |
| 2002/0095214 A1 | 7/2002 | Hyde | |
| 2002/0116006 A1 | 8/2002 | Cohen | |
| 2002/0147498 A1* | 10/2002 | Tallarida ................ A61B 90/11 623/20.14 | |
| 2003/0018337 A1* | 1/2003 | Davis ................ A61B 17/1655 606/80 | |
| 2003/0078668 A1 | 4/2003 | Michelson | |
| 2003/0100947 A1 | 5/2003 | Nadler et al. | |
| 2003/0144741 A1 | 7/2003 | King et al. | |
| 2003/0216669 A1 | 11/2003 | Lang et al. | |
| 2004/0098133 A1 | 5/2004 | Carignan et al. | |
| 2004/0147927 A1 | 7/2004 | Tsougarakis et al. | |
| 2004/0215203 A1 | 10/2004 | Michelson | |
| 2004/0267266 A1 | 12/2004 | Daniels et al. | |
| 2005/0149031 A1* | 7/2005 | Ciccone ................ A61B 17/864 606/280 | |
| 2005/0209694 A1 | 9/2005 | Loeb | |
| 2005/0222575 A1 | 10/2005 | Ciccone et al. | |
| 2005/0234467 A1 | 10/2005 | Rains | |
| 2006/0198877 A1 | 9/2006 | Steinwachs et al. | |
| 2006/0206208 A1* | 9/2006 | Michelson ........... A61B 17/861 623/17.11 | |
| 2006/0235539 A1 | 10/2006 | Blunn et al. | |
| 2006/0241594 A1 | 10/2006 | McCarthy et al. | |
| 2006/0247790 A1 | 11/2006 | McKay | |
| 2007/0021838 A1 | 1/2007 | Dugas et al. | |
| 2007/0100459 A1 | 5/2007 | Rhodes | |
| 2007/0159487 A1 | 7/2007 | Felt | |
| 2007/0233150 A1 | 10/2007 | Blain et al. | |
| 2007/0276501 A1 | 11/2007 | Betz et al. | |
| 2008/0051793 A1* | 2/2008 | Erickson ............. A61B 17/1671 606/279 | |
| 2008/0243127 A1 | 10/2008 | Lang et al. | |
| 2008/0281328 A1 | 11/2008 | Lang et al. | |
| 2009/0198291 A1* | 8/2009 | Kevin .................. A61B 17/863 606/305 | |
| 2009/0209962 A1 | 8/2009 | Jamali | |
| 2009/0270868 A1 | 10/2009 | Park et al. | |
| 2009/0318927 A1 | 12/2009 | Martin et al. | |
| 2010/0185201 A1 | 7/2010 | Kim | |
| 2010/0191310 A1 | 7/2010 | Bly | |
| 2010/0234850 A1 | 9/2010 | Dees, Jr. et al. | |
| 2011/0029093 A1 | 2/2011 | Bojarski et al. | |
| 2011/0054483 A1 | 3/2011 | Howlett et al. | |
| 2011/0087332 A1 | 4/2011 | Bojarski et al. | |
| 2011/0152869 A1 | 6/2011 | Ek et al. | |
| 2011/0166661 A1 | 7/2011 | Boileau et al. | |
| 2011/0238071 A1 | 9/2011 | Fernandez-Scoma | |
| 2012/0053588 A1 | 3/2012 | Lozier et al. | |
| 2012/0150030 A1 | 6/2012 | Reach, Jr. et al. | |
| 2012/0209394 A1 | 8/2012 | Bojarski et al. | |
| 2012/0271417 A1 | 10/2012 | Ek | |
| 2012/0316565 A1 | 12/2012 | Stark | |
| 2012/0330316 A1 | 12/2012 | Berelsman et al. | |
| 2012/0330317 A1 | 12/2012 | Berelsman et al. | |
| 2012/0330360 A1 | 12/2012 | Nishida | |
| 2013/0165939 A1 | 6/2013 | Ries et al. | |
| 2013/0172891 A1 | 7/2013 | Bake et al. | |
| 2013/0173228 A1 | 7/2013 | Bake et al. | |
| 2013/0184820 A1 | 7/2013 | Schwartz et al. | |
| 2013/0185927 A1 | 7/2013 | Bake et al. | |
| 2013/0211410 A1 | 8/2013 | Landes et al. | |
| 2013/0211531 A1 | 8/2013 | Steines et al. | |
| 2014/0142643 A1 | 5/2014 | Bake et al. | |
| 2014/0208578 A1 | 7/2014 | Linderman et al. | |
| 2014/0224070 A1 | 8/2014 | Bake et al. | |
| 2014/0243836 A1 | 8/2014 | Bake et al. | |
| 2014/0249781 A1 | 9/2014 | Bake et al. | |
| 2014/0277522 A1 | 9/2014 | Goldberg et al. | |
| 2015/0190151 A1 | 7/2015 | Budhabhatti et al. | |
| 2015/0230874 A1 | 8/2015 | Musuvathy et al. | |
| 2015/0320429 A1 | 11/2015 | Katrana et al. | |
| 2016/0089159 A1 | 3/2016 | Ardito et al. | |
| 2016/0100847 A1 | 4/2016 | Maxson | |
| 2016/0151076 A1 | 6/2016 | Bake et al. | |
| 2016/0199075 A1 | 7/2016 | Bake | |
| 2017/0100253 A1 | 4/2017 | Bake et al. | |
| 2017/0156890 A1 | 6/2017 | Bake et al. | |
| 2017/0172744 A1 | 6/2017 | Bake et al. | |
| 2017/0172747 A1 | 6/2017 | Bake et al. | |

FOREIGN PATENT DOCUMENTS

| | | |
|---|---|---|
| EP | 1753365 B1 | 10/2007 |
| EP | 1864629 A2 | 12/2007 |
| EP | 2138110 A2 | 12/2009 |
| EP | 2389899 A1 | 11/2011 |
| EP | 2389905 A1 | 11/2011 |
| EP | 2389905 B1 | 5/2012 |
| EP | 2685905 A1 | 1/2014 |
| JP | H8-502681 A | 3/1996 |
| JP | H10504217 A | 4/1998 |
| JP | 2008-539814 A | 11/2008 |
| WO | WO-94/09730 A1 | 5/1994 |
| WO | WO-96/24302 A1 | 8/1996 |
| WO | WO-2006/091686 A2 | 8/2006 |

(56) References Cited

FOREIGN PATENT DOCUMENTS

| WO | WO-2007/014164 A2 | 2/2007 |
|----|-------------------|--------|
| WO | WO-2008/098061 A2 | 8/2008 |
| WO | WO-2008/101090 A2 | 8/2008 |
| WO | WO-2008/138137 A1 | 11/2008 |
| WO | WO-2009/108591 A1 | 9/2009 |
| WO | WO-2009/111626 A2 | 9/2009 |
| WO | WO-2010/099357 A1 | 9/2010 |
| WO | WO-2011/063257 A1 | 5/2011 |
| WO | WO-2012/129018 A1 | 9/2012 |
| WO | WO-2012/143531 A1 | 10/2012 |
| WO | WO-2013/030371 A9 | 3/2013 |

OTHER PUBLICATIONS

Extended European Search Report dated Jun. 13, 2017 in European Patent Application No. 17155242.5.
Notice of Rejection dated Feb. 19, 2018 issued in corresponding Japanese patent application No. 2017-500889 (2 pages) and its English-language translation thereof (3 pages).
Notification of Reasons for Refusal dated Mar. 29, 2018 issued in corresponding Japanese patent application No. 2017-500881 (4 pages) and English-language translation thereof (5 pages).
Notification of Reasons for Refusal dated Sep. 20, 2018 issued in Japanese patent application No. 2017-500889 (2 pages) and its English-language translation thereof (3 pages).
Office Action dated Jan. 25, 2018 issued in U.S. Appl. No. 15/324,351 with double-patenting rejections on p. 2-5.
Office Action dated May 13, 2015 issued in corresponding European patent application No. 12 755 990.4 (6 pages).

\* cited by examiner

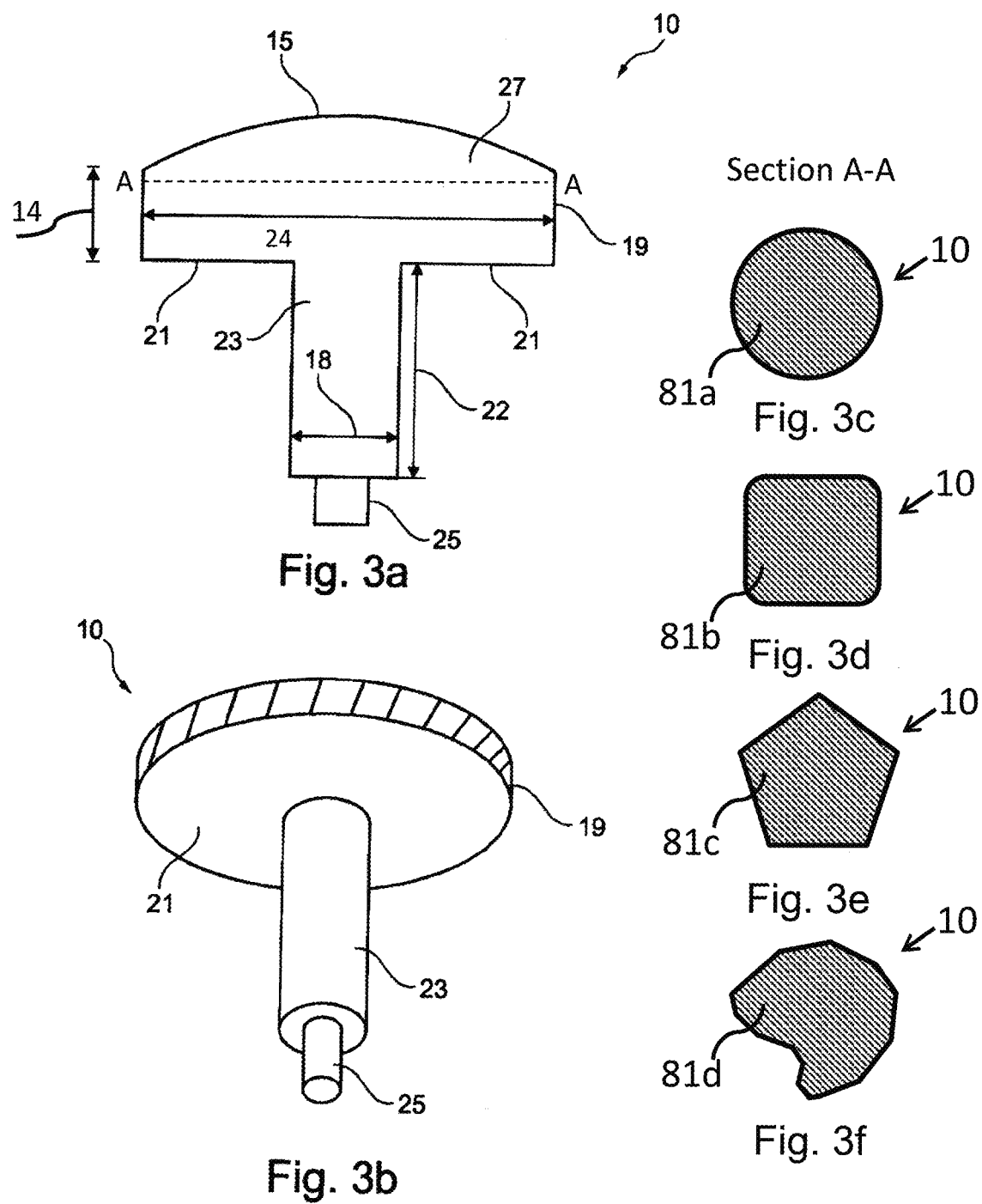

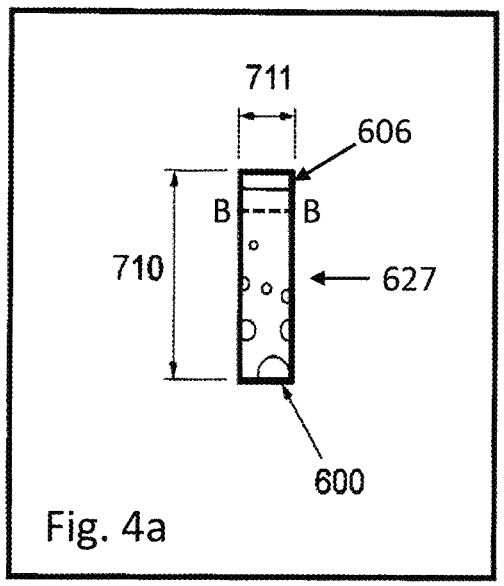
Fig. 4a
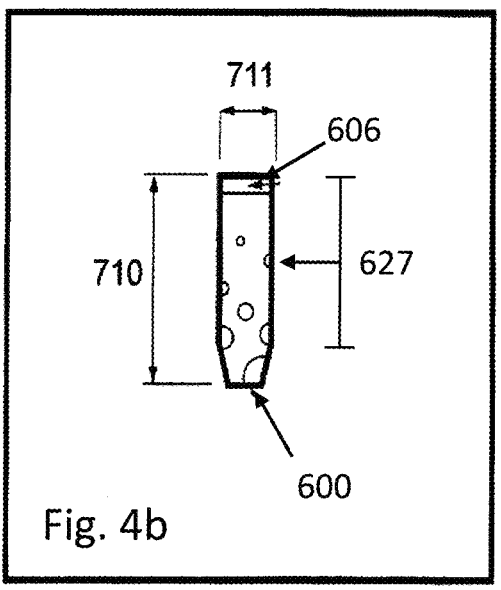
Fig. 4b
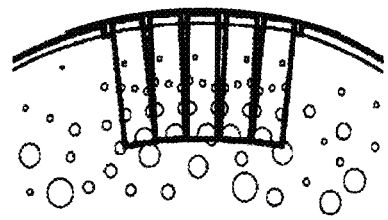
Fig. 4g
Fig. 4h
Section B-B
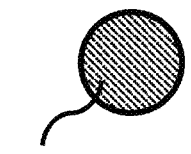 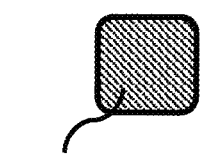  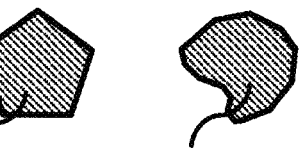
81e    81f    81g    81h
Fig. 4c    Fig. 4d    Fig. 4e    Fig. 4f

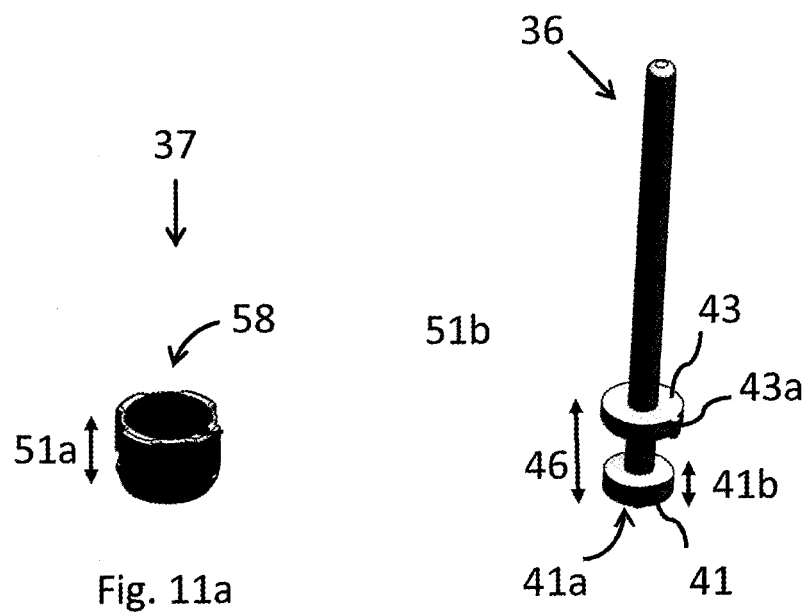
Fig. 11a
Fig. 11b
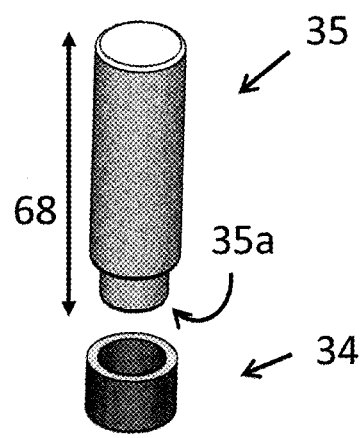
Fig. 12

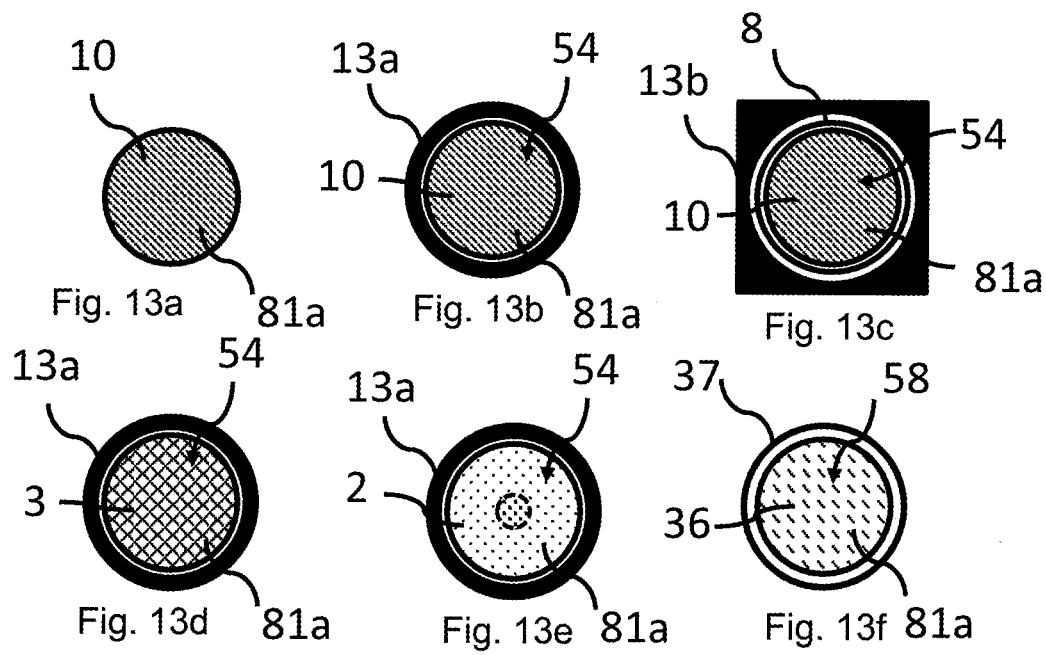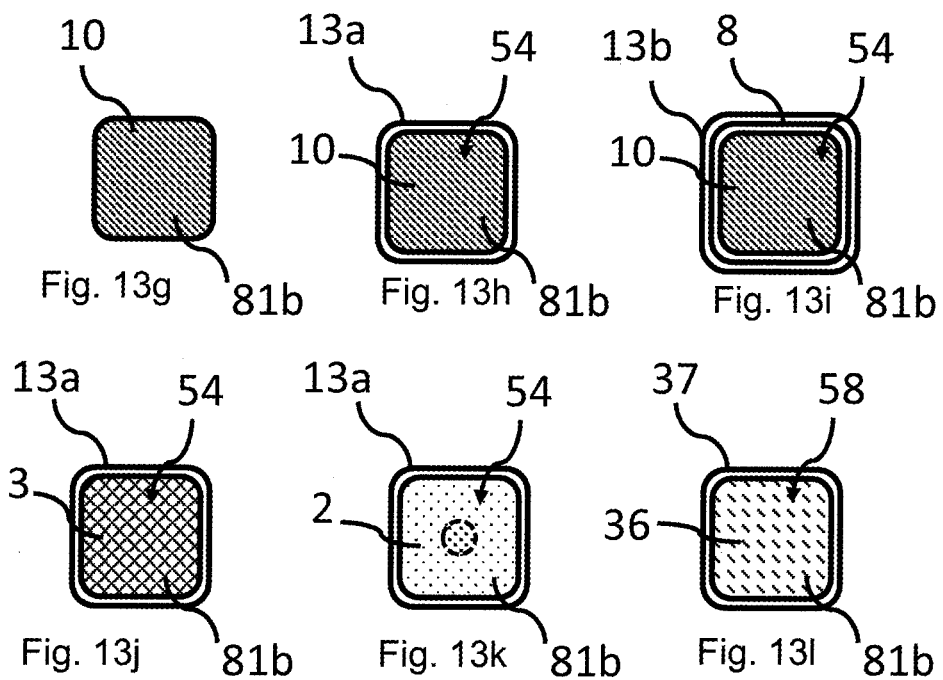

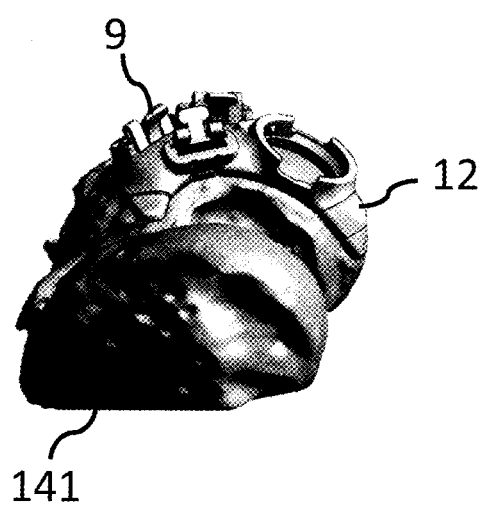
Fig. 14a
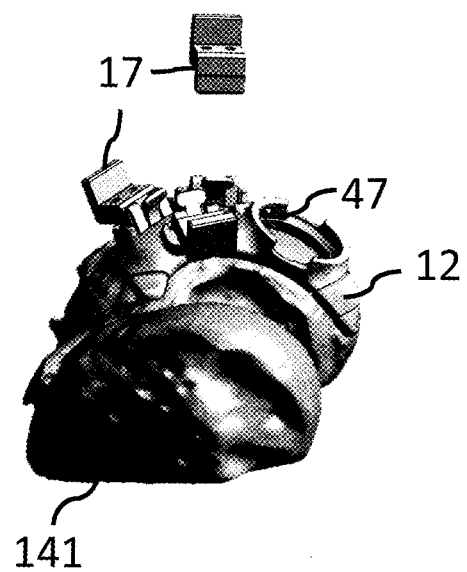
Fig. 14b
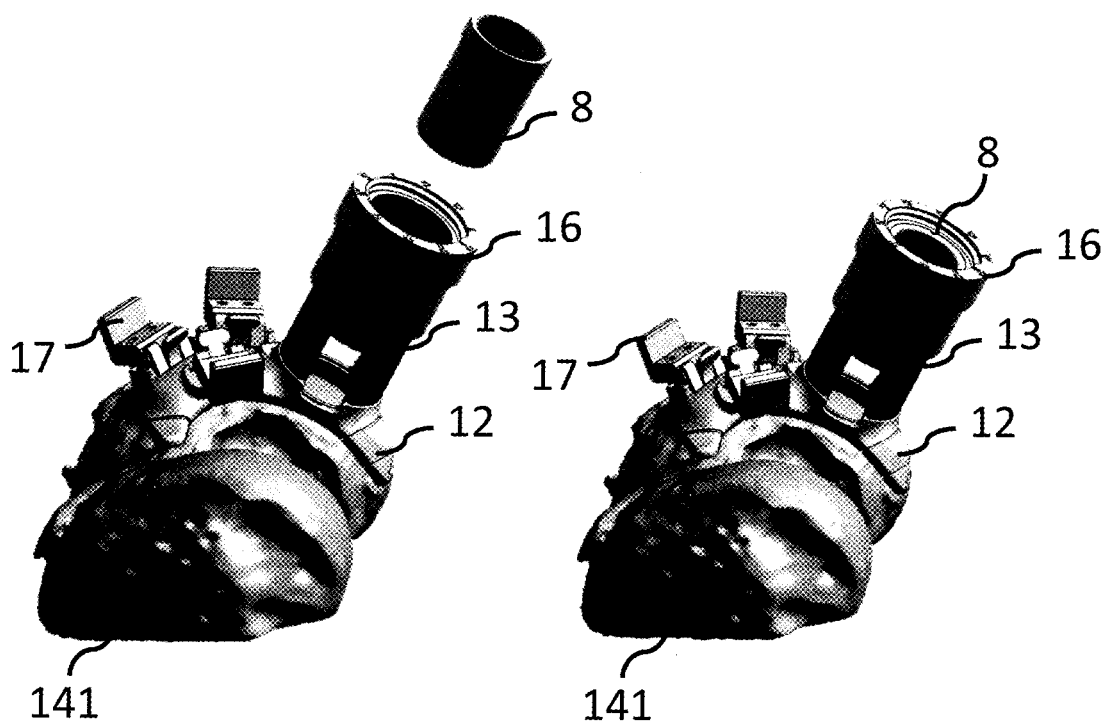
Fig. 14c
Fig. 14d

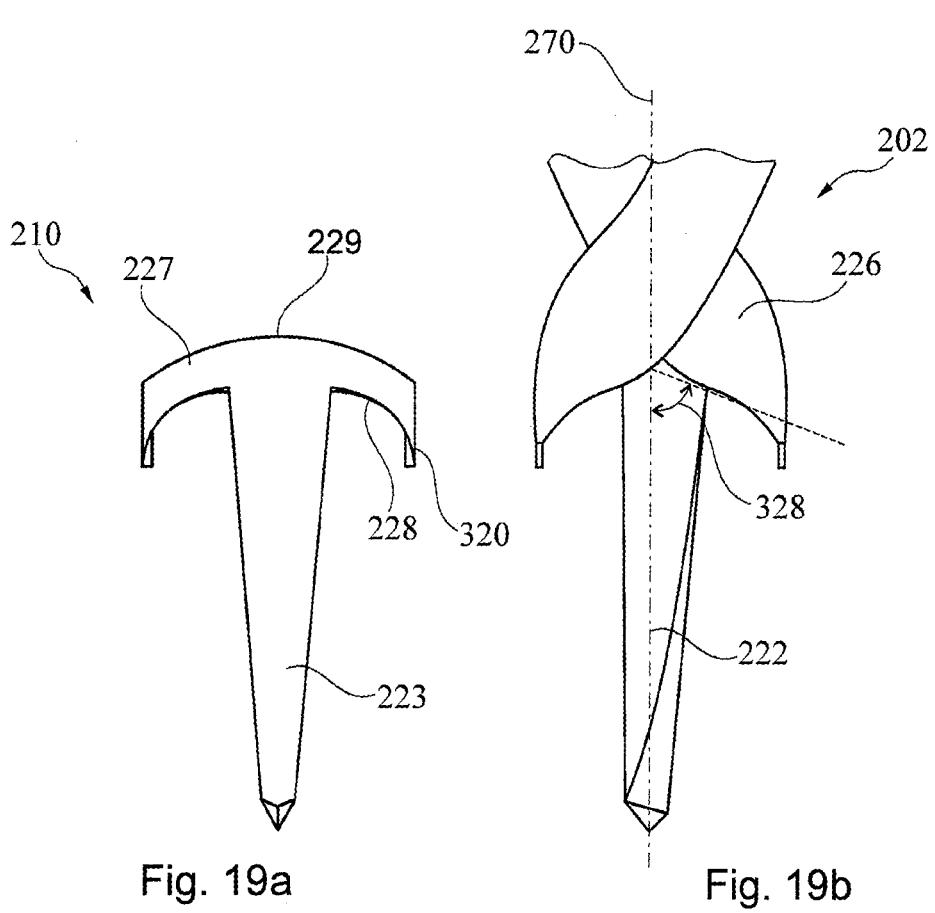

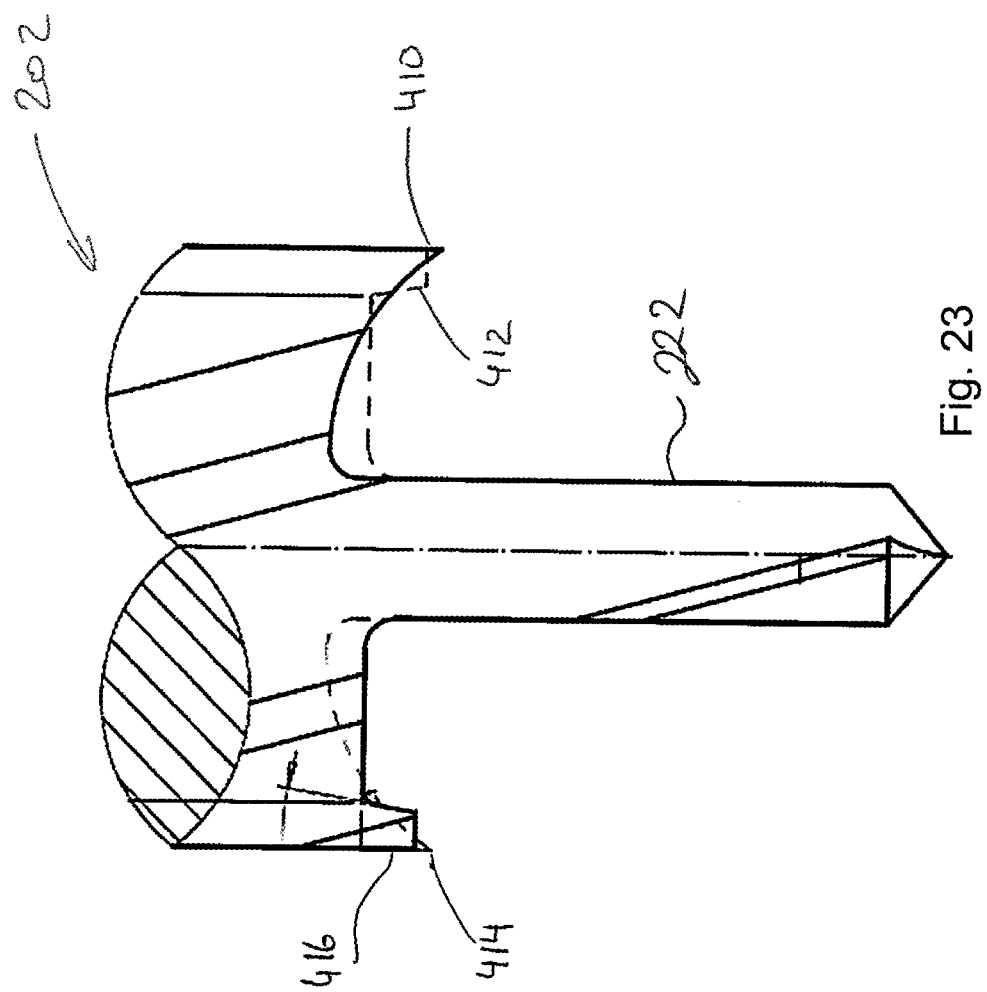

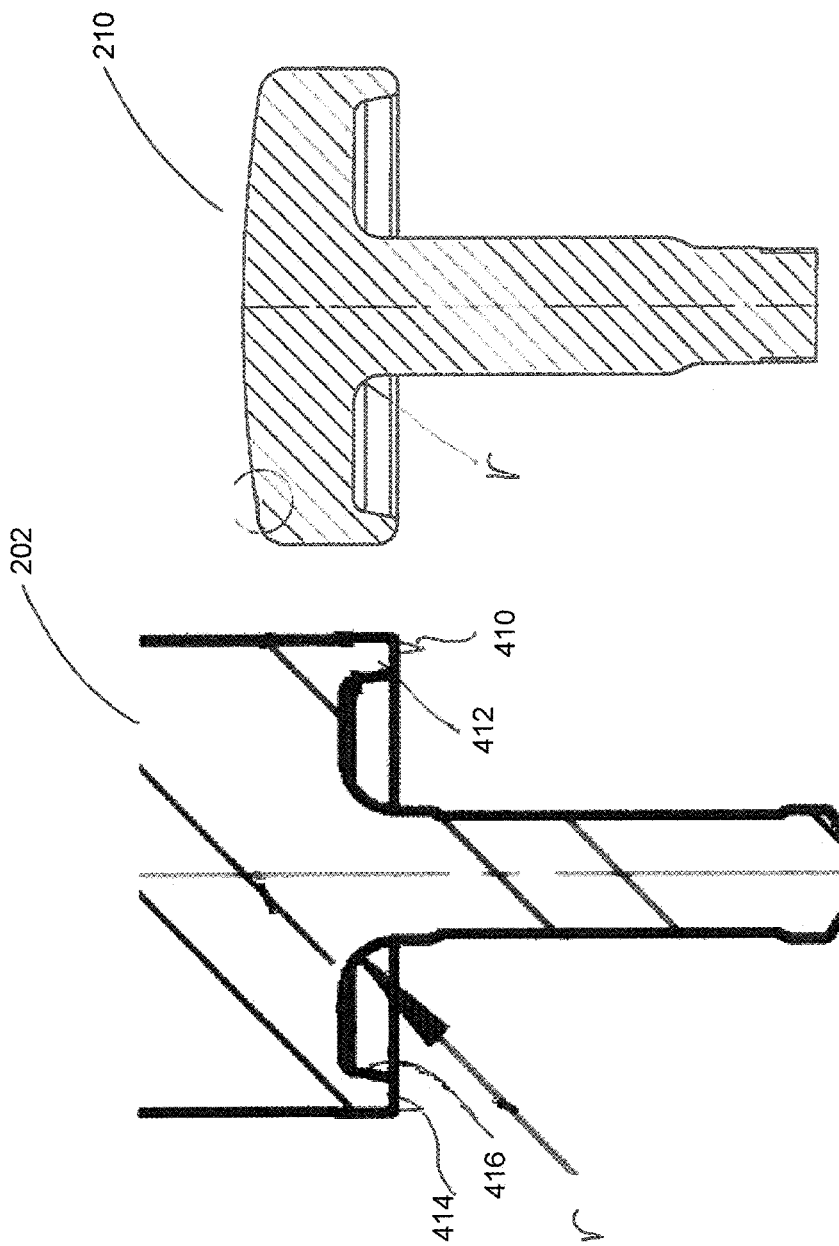

IMPLANT SPECIFIC DRILL BIT IN SURGICAL KIT FOR CARTILAGE REPAIR

CROSS-REFERENCE TO PRIOR APPLICATIONS

This application is a continuation of U.S. patent application Ser. No. 15/018,812, filed Feb. 8, 2016 (allowed), which is a continuation-in-part application of U.S. patent application Ser. No. 14/342,302, filed Apr. 11, 2014, now U.S. Pat. No. 9,254,196, issued Feb. 9, 2016, which is a § 371 National Stage Application of PCT International Application No. PCT/EP2012/067024 filed Aug. 31, 2012, which claims priority to European Patent Application No. 11179923.5 filed Sep. 2, 2011 and U.S. Provisional No. 61/530,497 filed Sep. 2, 2011, each of which is herein incorporated by reference in its entirety.

FIELD OF THE DISCLOSURE

This disclosure relates in general to the field of orthopedic surgery and to surgery kits, kits of tools and medical implants. More particularly the present disclosure relates to a modular surgical kit comprising a guide base and a guide body for use with a set of surgical tools. The surgical kit is to be used for replacement or repair of damaged cartilage at an articular surface in a joint such as a knee, hip, toe and shoulder. Embodiments of the disclosure relate to orthopedic drill bits used for forming bone cavities.

BACKGROUND

General Background

Pain and overuse disorders of the joints of the body is a common problem. For instance, one of the most important joints which are liable to wearing and disease is the knee. The knee provides support and mobility and is the largest and strongest joint in the body. Pain in the knee can be caused by for example injury, arthritis or infection. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibrocartilage. This means that damages of the cartilage gradually become worse. Along with injury/disease comes a problem with pain which results in handicap and loss of function. It is therefore important to have efficient means and methods for repairing damaged cartilage in knee joints.

Today's knee prostheses are successful in relieving pain but there is a limit in the lifetime of the prostheses of 10-15 years. The surgical operation is demanding and the convalescence time is often around 6-12 months. In many cases today, surgery is avoided if training and painkillers can reduce the pain. Prostheses are therefore foremost for elderly patients in great pain, at the end of the disease process; a totally destroyed joint. There are different kinds of prostheses, such as half prosthesis, total prosthesis and revision knee, the latter used after a prosthesis failure. The materials used in today's knee prostheses are often a combination of a metal and a polymeric material, but other materials such as ceramics have also been used. The size of knee prostheses makes it necessary to insert them through open surgery.

Other attempts practiced at various clinics around the world with the main objective to repair or rebuild cartilage include biological approaches such as micro fractures, cartilage cell transplantation (ACI), periost flap, and mosaic plasty surgery. In mosaicplasty surgery grafts, in the form of plugs or dowels of healthy cartilage and underlying bone are harvested from nonbearing parts of the join, i.e areas of low stress in the joint. Such plugs may be denoted osteochondral plugs. In related surgical techniques similarly shaped plugs as those of mosaicplasty, but made of artificial material, may be used. The plugs or dowels are inserted into drill holes made at the diseased or damaged site, such that they form a mosaic pattern of healthy cartilage at the surface of the joint. Osteochondral autograft transfer (OATS) is a technique similar to mosaicplasty but during the OATS procedure the plugs are usually larger, and therefore only one or two plugs are needed to fill the area of cartilage damage. A difficulty with both mosaicplasty and OATS is to make sure that the plugs are inserted such that they form an even surface. If the plugs are offset from their intended position, e.g. such that they are tilted or project over the surrounding cartilage tissue, it may cause increased wear and load on the joint, resulting in more pain for the patient. The biological treatments have shown only limited results this far, with implications such as high cost, risk of infection, risk of loosening, limited suitability for patients of different ages and the extent and location of damage. They do however have many advantages, especially for young patients who still are growing and who have better abilities for self-repair, if these difficulties can be overcome.

The advantages of implants have stimulated a further development of smaller implants that can be implanted with less invasive surgery. In this development there has also been an effort to achieve small joint implants, suitable for repair of a small cartilage injury that have a minimal influence on the surrounding parts of the joint. In the current development, such small implants are designed with an implant body that may be formed as a thin plate with a hard surface for facing the articulate side of the joint and a bone contacting surface for facing the bone below the damaged part of cartilage. The shape and the curvature of the articulate surface of the implant may be designed to be similar to the shape and the curvature of the part of the joint where the implant is inserted. Such implants are designed as mushrooms with an implant body or head and optionally with a peg or a rod projecting from the bone contacting side of the implant body for fastening the implant to the bone.

In the surgical operation of implanting small implants, including grafted plugs or artifical plugs used for mosaicplasty or OATS, it is critical that the implant is positioned in a precise manner. If the implant is offset from its intended position it may cause increased wear or load on the joint. For example, if the implant is tilted this may result in an edge that projects above the cartilage surface and causes wear on the opposing cartilage in the joint. Another example is when the implant is placed in a position with the surface of the implant projecting above the surface of the cartilage causing the joint to articulate in an uneven manner and increasing the load on an opposing point of the joint. For the patient, also small misplacements or deviations from an ideal position may result in pain, longer time for convalescence or even a surgical operation being done in vain and making it more difficult to repair the damage in the joint. A large burden is therefore placed on the surgeon not to misplace or misfit the implant. In order to support the surgeon during the implant surgery and to improve the positioning of the implant various tools and guides that support the surgical procedure have been developed.

Specific Background

During cartilage repair in a joint, different methods are known today for repair of cartilage damages. One example is replacing damaged cartilage and thereby repairing a part, namely the damaged part, of the cartilage in the joint instead of replacing the whole joint. This method, replacing a part of the cartilage in the joint using an implant, requires high precision tools. During such a repair it is important that the replacement is well fitted in the joint otherwise the implant will start to move and the repair in the joint will not last for long. The instruments on the market today are not user friendly and require much skills of the surgeon. Several instruments are needed for forming a recess for an implant and may lead to that there is lack of fit for the implant due to the several steps needed for making a recess. There is a need for improved instrumentation during these sorts of cartilage repairs. Improved instrumentation which is easy to use, and which gives the same result without dependence on which surgeon who is using them. It is also important that the instruments allow for short implantation procedures.

Some of the surgical tools developed for implant surgery include guide tools having a channel or similar through which the surgical tools and/or the implant are guided throughout the surgery. Often these guide tools are rather bulky and placed over the damaged site of the cartilage such that it is difficult for the surgeon to see the site of implantation during surgery. Also it may be difficult to remove debris and waste that is generated at the implantation site during surgery. In order for the surgeon to be able to inspect the implantation site and/or remove such surgery the guide tool has to be removed from the surgical site in the joint. There is a need for a surgical kit for replacement or repair of damaged cartilage at an articular surface in a joint that guides the surgeon, improves the positioning of the implant or the grated or artificial plugs used for mosaicplasty or OATS, and that facilitates inspection of the implantation site and removal of debris during surgery.

Prior Art

Examples of prior art disclosing smaller implants and tools for replacement of damaged cartilage are shown in:

WO2007/014164 A2 describes a kit comprising a plurality of small joint implants having different predetermined shapes described as circular, oval, L-shaped and triangular and tools for placing the implants and a method for placing the implant in a joint, e.g. in the knee or other joints where there is a need for repair of a cartilage and/or bone damage. In this piece of prior art each implant shape has a specific guide tool which corresponds to the shape of the implant.

The cartilage damage is repaired by choosing the most suitable implant from the different shapes mentioned above. The corresponding guide tool is selected and is used for faster reaming of the area where the implant is to be placed. A drill is used for drilling a hole to accept the post extending from the bone contacting side of the implant. In the end, the implant is placed on the area reamed or drilled out for the implant. Although it is the intention that the guide tool shall be used for the preparation of the placement of the implant it is also said that the use of the guide tool is optional, see passage sections [019, 020].

US20030216669 A1 Shows methods and compositions for producing articular repair material used for repairing an articular surface. The method for designing an articular implant comprises; taking an image of the joint, reconstructing dimensions of the diseased cartilage surface to correspond to normal cartilage and designing the medical implant accordingly. This prior art also shows a surgical assistance device or surgical tool for preparing the joint to receive an implant. The surgical tool comprises of one or more surfaces or members that conform to the shape of the articular surfaces of the joint. It can include apertures, slots and/or holes that can accommodate surgical instruments such as drills and saws. (see claim 18, [0029], [175] FIG. 13, 15, 16), and thus may also be designed and used to control drill alignment, depth and width, for example when preparing a site to receive an implant [0179]. The tool may be single-use or reusable [181]. These surgical tools (devices) can also be used to remove an area of diseased cartilage and underlying bone or an area slightly larger than the diseased cartilage and underlying bone [0182].

EP 1 698 307 A1 discloses an instrument for removing cartilage and introducing an implantable nonwowen into cartilage. The instrument may further comprise a cartilage puncher having a channel through which further instruments, such as surgical spoons or curettes, can be guided to the cartilage defect ([0028-0029]).

WO2008098061 A2 also shows examples of small articular surface implants and tools for placement of the implants. The tools and the implant are used to repair damaged articular cartilage areas.

WO2006091686 A2 Shows a small implant for replacing a portion of an articular surface (see the abstract). The implant is placed using a rotating excision tool (see page 8 line 25) and the implant is selected from a set (see page 10 line 22-23).

WO 2009111626 Shows implants for altering wear patterns of articular surfaces of joints (see [00190]) and a device and a method for repair of articular surfaces, in for example a knee. The implants and methods may replace all or a portion of the articular surface and achieve an anatomic or near anatomic fit with the surrounding structures and tissues, the techniques described herein allow for the customization of the implant to suit a particular subject, the implant is a mirror image of the articular surface, see[0057]-[0058]. The implants are selected from predetermined shaped and their location can be optimized for the patients wear pattern and the wear patterns are assessed by for example MRI [0061]-[0063], [0072]. The tools used for placement of the implants are selected depending on MRI images but not created depending on the images [00211].

WO2008101090 A2 shows a method for making a large implant suitable for a joint. The 3D surface of the joint implant is determined using MRI or CT depicting the damaged that is to be repaired.

US2006/0198877 A1 shows a medical instrument for autologous chondrocyte transplantation.

WO2009/108591 A1 shows a method and tools for repairing an articular cartilage defect and also an implant.

US6306142B1 shows a system and tools for transplanting a bone plug from a donor site to a recipient site.

US 2003/0100947 A1 shows a device for repairing articular cartilage defects.

EP2389905B1 describes a method for designing a surgical kit comprising a drill bit for drilling. Several instruments are needed for making the recess for an implant comprising an extending post.

OBJECT OF THE DISCLOSURE

General Object

The general object of the disclosure is to solve the problem of providing means that aid the implantation of a cartilage replacement implant, including grafted or artificial plugs used for mosaicplasty or OATS, into the articular surface of a joint, aiding and facilitating the work for the surgeon and improving the positioning of the implant in order to generate optimal repair of damaged tissue and cause minimum damage to the surrounding tissue.

The disclosure further seeks to solve the partial problems of facilitating inspection of the implantation site and removal of debris during surgery.

A further object of the disclosure is to solve the problem of designing improved instruments for use during replacement of damaged cartilage. Another object is to provide the design of an implant specific drill bit makes the surgical operation safer and results in better fitting implants.

SUMMARY OF THE DISCLOSURE

The present disclosure provides a drill tool for implant surgery comprising a first drill part 222 having a first, smaller diameter for drilling a recess for an implant post, a second drill part 220 having a second, larger diameter for drilling a recess for an implant hat, said second drill part having one or more shape cutting edges 228 and one or more sharp pre-cutting edges 410 extending beyond said one or more shape cutting edges 228. In embodiments, at least one of the one or more sharp pre-cutting edges extend beyond the implant hat, in order to provide a gap under the implant. In embodiments, at least one of the one or more shape cutting edges 228 comprises a protruding flange 320. In embodiments, the protruding flange 320 protrudes from the shape cutting edge surface 228 with a length 324 of approximately 0.3-3 mm and a width 326 of 0.3-1.5 mm or 0.3-2 mm. The pre-cutting edge 410 may e.g. have a length 224 of 0.3-3 mm protruding from the shape cutting edge 228 and/or a width 225 of 0.3-2.0 mm or 0.3-2.0 mm. The angle 328 between the shape cutting edge 228 and the longitudinal y-axis 270 of the implant specific drill bit 202 may e.g. be designed to be 90° or less or e.g. 80° or less or 70° or less.

The present disclosure further provides an implant specific drill bit 202 comprising:
- a drill and bone remover body 220 having a proximal end and a distal end and a longitudinal axis extending between the proximal end and the distal end;
- a bone remover part 226 located in one end of the bone remover body 220; and
- a central drill part 222 protruding from said bone remover part 226;
- wherein said bone remover part 226 comprises one or more shape cutting edges 228 placed peripherally around the central drill part 222, wherein said one or more shape cutting edges 228 comprises one or more sharp pre-cutting edges extending beyond said one or more shape cutting edges.

In embodiments, the one or more shape cutting edges 228 comprise a flat surface or a surface which further comprises flanges 320.

The present disclosure further provides a modular surgical kit comprising a guide base and a guide body for use with a set of tools and a method for replacing a portion, e.g. diseased area and/or area slightly larger than disease area, of a joint, e.g. cartilage and/or bone, with an implant or with one or more artificial or grafted bone and cartilage plugs, such as those used for mosaicplasty or OATS. The modular surgical kit may also comprise the set of tools. The modular surgical kit is arranged to achieve a near anatomic fit of the implant with the surrounding structures and tissues as well as facilitating to surgical procedure.

The present disclosure further provides a modular surgical kit for repair of diseased cartilage at an articulating surface of a joint. It is for use with a medical implant, a grafted plug, or an artificial plug that has an implant body with a predetermined cross-sectional profile. The modular surgical kit comprises a guide base with a positioning body and a guide hole through the positioning body. The positioning body has a cartilage contact surface that is designed to fit the contour of cartilage or subchondral bone in the joint in a predetermined area surrounding the site of diseased cartilage. The guide hole has a muzzle on the cartilage contact surface at a position corresponding to the site of the diseased cartilage.

The modular surgical kit further comprises a guide body with a guide channel. The guide channel has a cross-sectional profile that is designed to correspond to the cross-sectional profile of the implant body and also has a muzzle.

Furthermore, the guide base, e.g. the positioning body comprises means for releasably connecting to the guide body. When connected, the guide channel is positioned in relation to the positioning body such that its muzzle emanates at a site corresponding to the site of implantation into the bone.

In one embodiment of the modular surgical kit the cartilage contact surface is custom designed to fit the contour of the cartilage or subchondral bone of a specific patient. In another embodiment the cartilage contact surface is designed to fit the contour of the cartilage or subchondral bone of an average patient.

In one embodiment of the modular surgical kit, for use e.g. in mosaicplasty or OATS surgery, the guide body comprises at least two guide channels. Each guide channel has a cross-sectional profile that is designed to correspond to the respective cross-sectional profile of at least two implant bodies.

In a further embodiment of the modular surgical kit the guide channel, having a cross-sectional profile that is designed to correspond to the cross-sectional profile of the implant body, is provided by a guide insert that is designed to fit in the guide body.

In still another embodiment the modular surgical kit further comprises a drill adjustment device that is arranged to enable adjustment of the drill depth e.g. in certain length intervals.

In one embodiment the positioning body is arranged with at least one breakage means for enabling easy removal of part of the positioning body by tearing, fracturing or similar breakage. Such means may for example be provided by grooves, slots or perforations or other weakening of the structure.

The positioning body may also be arranged with at least one attachment means for enabling easy attachment of adaptors, pins and other devices used during surgery, e.g. by snap fit. The modular kit may also further comprise adaptors that fit the attachment means, for enabling flexible attachment of pins and other devices.

In one embodiment the modular surgical kit further comprises an insert tool with a cross-sectional profile that is designed to correspond to the cross-sectional profile of the guide channel, with a tolerance enabling the insert tool to slide within the guide channel.

Such insert tool may be a cartilage cutting tool that has a cross-sectional profile that is designed to correspond to the cross-sectional profile of the guide channel, with a tolerance enabling the cartilage cutting tool to slide within the guide channel. The cartilage cutting tool comprises a cutting blade with sharp cutting edges that are able to cut the cartilage in a shape that substantially corresponds to the cross-section of the implant body.

The insert tool is in another embodiment a drill and bone remover having a drill and bone remover body with a cross-sectional profile that is designed to correspond to the cross-sectional profile of the guide channel, with a tolerance enabling the drill and bone remover to slide within the guide channel. The drill and bone remover may comprise a central drill, for drilling a bore to receive the extending post of the implant, and a bone remover, for cutting a recess in the bone to receive the implant body of the implant.

The insert tool may further be a mandrel having a mandrel surface that is designed to fit the articulate surface of the implant. The mandrel also has a cross-sectional profile that is designed to correspond to the cross-sectional profile of the guide channel, with a tolerance enabling the mandrel to slide within the guide channel.

In one embodiment the surgical kit further comprises an implant dummy having an implant element that is designed to match the implant body and having a lower surface that is a replica of the bone contact surface of the implant, but comprising no extending post. The surgical kit may further comprise a dummy reference that is arranged to fit to, and possibly releasably attach to, the guide hole of the guide base. It is arranged to receive the implant dummy, by being provided with a channel.

Embodiments provide an implant specific drill bit.

The present disclosure further provides a design method designing an implant specific drill bit 202 comprising steps:
a. determining or selecting a size and shape of an orthopedic implant 210 comprising a circular shaped implant body or hat 227 and a centrally placed circular shaped extending post 223 protruding from the bone contacting surface 238 in a longitudinal y-axis 260 direction of the implant 210; and
b. selecting design parameters for the implant specific drill bit 202 by;
selecting the width 240 of the broadest part of the bone remover 226 in a side view to correspond to, or to be slightly smaller than, the diameter 250 of the implant body or hat 227 of the specific implant 210 that is to be implanted;
selecting the rotational volume and the length 272 of the central drill part 222 to correspond to, or to be slightly smaller than, the diameter of the extending post 223 of the specific implant 210 that is to be implanted;
selecting the curvature of the one or more shape cutting edges 228 that is placed anywhere peripherally around or surrounding the central drill part 222 of the implant specific drill bit 202 to correspond to the curvature of the bone contacting surface 238 of the implant.

In embodiments, the selection of design parameters for the implant specific drill bit 202 further comprises adding one or more sharp pre-cutting edges 410, 414 extending beyond said one or more shape cutting edges 228.

In embodiments, the one or more sharp pre-cutting edges 410, 414 are designed to extend beyond the implant hat 227, in order to provide a gap under the implant hat 227.

In one embodiment the design method according to the present disclosure for designing the implant specific drill bit comprises determining the size and shape of said implant so that it may either be performed by:

selecting implants from a kit of implants of different predetermined sizes; or
by individually designing the size and shape of an implant;
wherein the size and shape of the selected implant is corresponding in large or partly or substantially to the size and shape of a cartilage damage in a specific patient.

A design method according to any of the preceding claims wherein said shape cutting edge 228 in side view is designed to correspond to the shape of at least one side of the bone contacting surface 238 in a cross-sectional view of the specific implant 210; and wherein the bone contacting surface (38) is substantially flat or a bone contacting surface 238 which comprises an protruding anchoring ring portion 236.

In embodiments, the selection of design parameters for the implant specific drill bit 202 further comprises providing the shape cutting edge 228 with at least one protruding flange 320 corresponding to a protruding anchoring ring portion 236.

Further varieties of the design method according to the disclosure comprising any of the following optional, individual or combinable aspects.

A design method wherein the volume of the part of the designed implant specific drill bit 202 which corresponds to fit the implant 210 is 0.1-5% smaller than the volume of the implant (10) to be implanted, allowing for press fit of the implant 210 placed in the recess made by the implant specific drill bit 202 according to the disclosure.

A design method wherein the cutting edge comprises at least one flange 320.

A design method wherein the flange has a length 224 of 0.3-3 mm protruding from the shape cutting edge 228 and/or a width 225 of 0.3-2.0 mm or 0.3-2.0 mm corresponding to the length 235 in a cross-sectional view of the anchoring ring portion 236 of an implant 210.

A design method wherein the angle 328 between the shape cutting edge 228 and the longitudinal y-axis 270 of the implant specific drill bit 202 is designed to be 90° or less or for example 80° or less or 70° or less based on the selected specific implant and its corresponding angle.

A design method wherein the length 272 of the central drill part 222 of the implant specific drill bit is designed to be 2-300 mm corresponding to or slightly longer, or 1-5% longer than the length 282 of the extending post 223 of an specific implant 210.

An implant specific drill bit 202 made due to the design method used for designing the product for producing bone cavities for receiving orthopedic implants according to the disclosure wherein, said drill bit 202 comprises:
a drill and bone remover body 220 having a proximal end and a distal end and a longitudinal axis extending between the proximal end and the distal end; and
a bone remover part 226 located in one end of the bone remover body 220; and
a central drill part 222 protruding from said bone remover part 226;
wherein said bone remover part 226 comprises one or more shape cutting edges 228 placed peripherally around the central drill part 222, wherein said one or more shape cutting edges (228) comprises one or more sharp pre-cutting edges (410, 414) extending beyond said one or more shape cutting edges (228).

An implant specific drill bit 202 wherein the bone remover part 226 comprises a flat surface or a surface which further comprises flanges 320.

A kit comprising an implant specific drill bit 202 and an implant 210, wherein said implant specific drill bit 202 is designed according to any one of the design methods described above to correspond to the size and shape of said implant 210.

A implant specific drill bit 202 or a drill and bone remover 202 according to the disclosure that is used to drill a hole in the bone at the site of cartilage damage, for fastening of the extending post 223 of the implant 210 in the bone tissue, and simultaneously create a recess in the bone tissue at the site where the implant body 227 is to be received. The drill and bone remover 202 comprises a drill and bone remover body 220, a central drill 222 and a bone remover 226. The central drill 222 extends from the center of the drill and bone remover body 220, i.e. corresponding to the position of a centrally placed extending post 223 on an implant 210 having a circular implant body 227. The diameter of the central drill 222 is the same as, or slightly smaller than, the diameter of the extending post 223 of the implant 210 that is to be implanted. The bone remover 226 has a cutting edge that is placed peripherally around the central drill 222. The diameter of the bone remover 226 is the same as, or slightly smaller than, the diameter of the implant body 227 of the implant 210 that is to be implanted, thus creating a recess that matches the implant body, in which the implant body can be received. The cutting edge of the bone remover 226 is hard enough for cutting or carving bone. It may be made of materials such as stainless steel.

The drill and bone remover body 220 may be designed to fit the inside of the guide channel of the guide body of a guide tool, with a slight tolerance to allow a sliding movement of the drill and bone remover 202 in the guide channel. In other words, the cross-sectional profile of the drill and bone remover body 220 matches the cross-sectional profile of the guide channel as well as the of the implant 210. The fit ensures the correct, desired placement of the drill and bone remover 202 on the cartilage surface and thus ensures the precise direction and placement of the drill hole for the extending post 223, as well as the recess for the implant body 227, in the bone.

The drill and bone remover 202 may also be equipped with a depth gauge 207. The depth gauge 207 of the drill and bone remover determines the depth of the created drill hole as well as the recess for the implant body 227. The depth gauge 207 has a cross-sectional profile that is larger than the cross sectional profile of the guide channel. The depth gauge 207 will, during the surgical procedure, rest against the top of the guide body and/or drill adjustment device 16, thus preventing the drill and bone remover 202 to drill/carve/cut deeper into the bone. The distance between the tip of the cutting edge of the cutter and the depth gauge 207, and the relation between that distance and the length of the guide channel, will determine the depth that the is allowed to go into the cartilage and/or bone. The depth gauge 207 may be arranged such that that distance is adjustable. In a more preferred embodiment the distance is fixed and instead the drill/cut/carve depth is adjusted by adjusting the length 31 through the drill adjustment device 16.

BRIEF DESCRIPTION OF THE FIGURES

The present disclosure will be further explained below with reference to the accompanying drawings, in which:

FIGS. 3a-b shows an exemplifying embodiment of an implant.

FIGS. 3c-f show exemplifying cross-sectional profiles of such implant.

FIGS. 4a-b show an exemplifying embodiment of a grafted plug.

FIGS. 4c-f show exemplifying cross-sectional profiles of such grafted plug.

FIGS. 4g-h show such grafted plugs implanted into bone by use of mosaicplasty surgery.

FIG. 11a shows an exemplifying embodiment of a dummy reference.

FIG. 11b and an implant dummy.

FIG. 12 shows an exemplifying embodiment of a mandrel.

FIGS. 13a-l show exemplifying embodiments of the cross-sectional profiles of an implant and tools of the modular surgical kit.

FIG. 19a schematically illustrates an implant specific drill bit according to an exemplified embodiment.

FIG. 19b schematically illustrates an implant for implantation according to an exemplified embodiment.

FIG. 23 shows an embodiment of a drill tool with sharp pre-cutting edges and shark fin shape forming edges.

FIGS. 25a and 25b illustrate an embodiment of a drill tool and implant, and show the corresponding shapes of the lower part of the drill tool and the bone contacting part of an implant.

DETAILED DESCRIPTION

Introduction

This disclosure concerns a surgical kit for use in orthopedic surgery. A surgical kit according to the disclosure comprises a set of tools for the implantation of an implant, or one or more grafted plugs or artificial plugs that replaces damaged cartilage in a joint.

Figure 2:
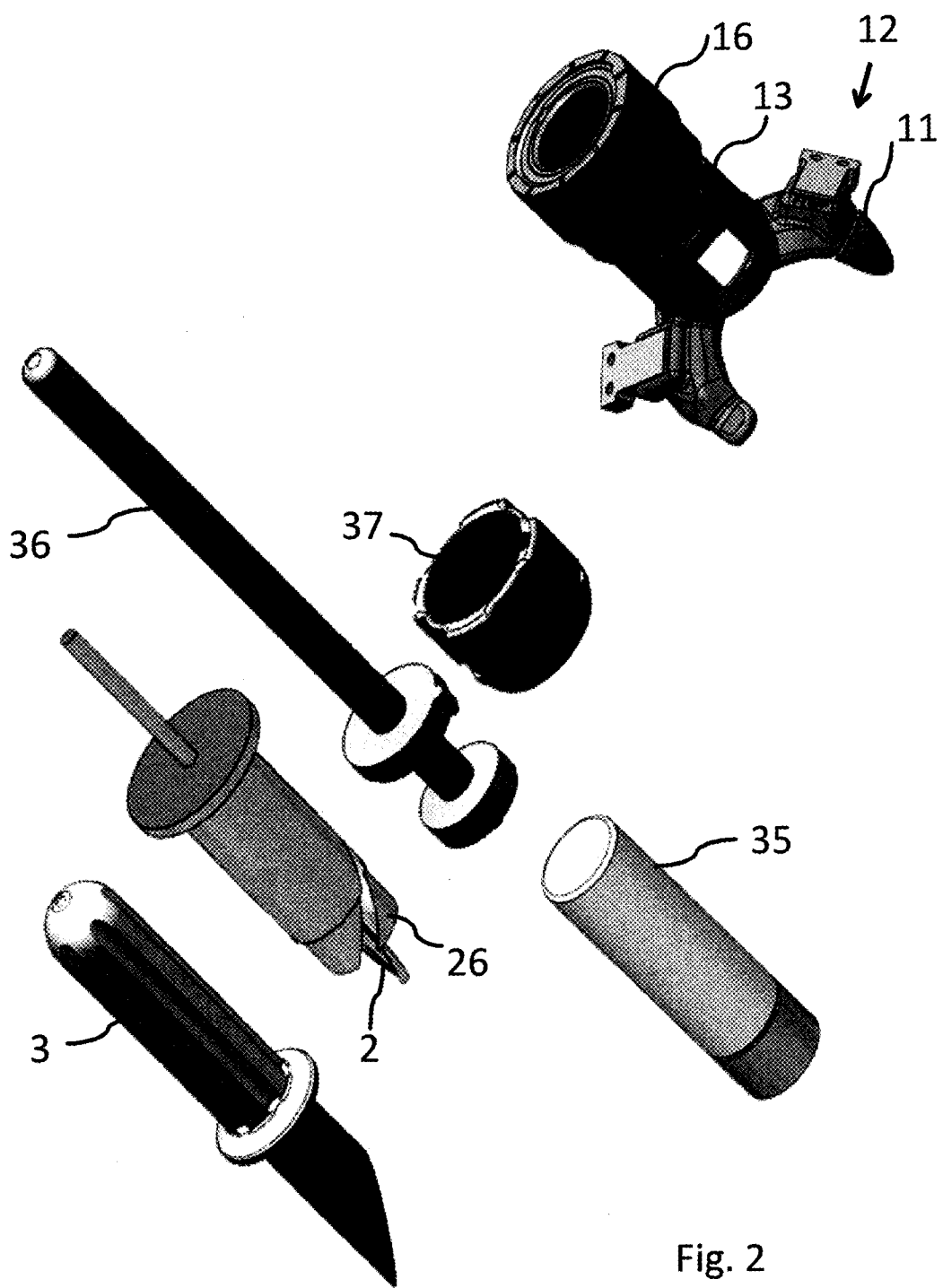
FIG. 2 shows a surgical kit according to one embodiment, exemplified by a surgical kit for a knee, the surgical kit comprising a guide base, a guide body and a set of tools.

FIG. 2 shows a surgical kit according to one embodiment of the present disclosure, for use in repair of damaged cartilage in a knee joint. The surgical kit comprises tools that are adapted to an implant and to a joint; a guide base 12 with a positioning body 11 and, releasably attached thereto, a guide body 13. A drill adjustment device 16 fitting to the guide body 13 may also be included in the kit. Further the surgical kit may comprise insert tools, for example a cartilage cutting tool 3: a drill 2, in this exemplifying embodiment equipped also with a bone remover 26, an implant dummy 36, a dummy reference 37 and/or a mandrel 35. Optionally, the kit may also comprise the implant to be implanted by use of the surgical kit.

The implant and the set of tools according to the disclosure are preferably individually designed for a person's joint. The implant and the set of tools are also optionally individually designed for a specific person's cartilage individual injury.

Exemplifying embodiments of the disclosure are shown herein which are especially adapted for cartilage replacement at the femur of a knee joint and at the joint of a toe. The disclosure may however, also have other useful applications, such as for cartilage replacement at an articulating surface at any other joint in the body, e.g. elbow, ankle, finger, hip and shoulder.

The Surgical Kit

This disclosure provides a surgical kit where the successful implant insertion is less depending on the skills of the surgeon compared to previously known methods and which facilitates inspection of the surgical procedure as well as removal of wear and debris during the surgery. This disclosure provides preferably individually designed tools and implant. Due to the design and the function of both tools and implant the surgical kit gives improved implantation precision and a precise desired placement of the implant in the joint every time. The precision of the surgery is "built in" into the design of the tools.

The surgical kit of the disclosure leads to shorter learning curves for the surgeon since the surgical kit facilitates for quick, simple and reproducible surgery.

In one exemplifying embodiment the implant is intended for replacing damaged cartilage in a knee. The site where the implant is to be implanted according to the disclosure is an articular cartilage surface including, for example, the lateral femoral chondral (LFC) surfaces, medial femoral chondral (MFC) surfaces, trochlea surfaces, patella surfaces, tibia surfaces (e.g. surfaces of the tuberosities of the tibia), and combinations and portions thereof. For example implants may be placed on any one of these surfaces.

In another exemplifying embodiment the implant is intended for replacing damaged cartilage in a toe, for example on the cartilage surfaces between the metatarsals and the proximal phalanges bones in a toe.

In a further exemplifying embodiment the implant is intended for replacing damaged cartilage in a shoulder, for example on the articulation surfaces between the head of the humerus and the lateral scapula (specifically—the glenoid fossa of the scapula).

The implant is inserted through a small open surgery operation using a tool kit where the tools in the tool kits are preferably individually designed or tailor/custom made for the person who suffers from the injury. This leads to decreased suffering of the patient and is economically favorable since it leads to shorter convalescence time and less time for the patient at the hospital. By using this optionally individually designed surgery kit the implant insertion will be optimal and thus misalignment which is one of the problems associated with the common methods used today can be avoided.

Using the surgical kit according to the disclosure, small cartilage damages will require small implants and in this way combined with the design of the guide tool, a surgical operation with little tissue damage, a small open surgery, is needed for the person suffering from a knee injury. This gives the effect that minimal modifications on the underlying bone and surrounding tissue are required when preparing for the implant surgery. Using implants according to the present disclosure makes it possible to repair cartilage defects at a much earlier stage than previously. This early replacement of damaged cartilage may postpone or prevent osteoarthritis.

The object of the disclosure is to solve the problem of repairing damaged, injured or diseased cartilage in knees, toes, elbows or shoulders by providing an implant that will have better placement and thus a seamless placement in the cartilage.

The benefits from the implant according to the disclosure are relief from pain and swelling in the joint and also the restoration of a smooth, continuous articulating surface. The implant and the tool kit of the present disclosure also facilitates for the return to normal activity with rapid recovery time, possibility to postpone or avoid total knee replacement surgery. A less traumatic surgery procedure is used and potentially faster recovery after surgery.

Implants

The surgical kit of the present disclosure may be used for implantation of for example small implants and of bone and cartilage plugs, such as osteochondral plugs, or artificial plugs used in mosaicplasty or OATS. Examples of implants to be used with the surgical kit of the disclosure will be given below. The kit may however be used with any implant having an implant body with a cross-sectional profile that corresponds to the cross-sectional profile the guide channel of the guide body 13 (see below).

Small Implant

FIGS. 3a-3b shows an embodiment of a medical implant 10 that may be used with a surgical kit according to the present disclosure. The implant comprises an implant body 27 and an extending post 23. The implant body 27 has an articulate surface (first surface) 15 configured to face the articulating part of the joint and a bone contact surface (second surface) 21 configured to face bone structure in the joint. An extending post 23 extends from the bone contact surface 21. Between the articulate surface 15 and the bone contact surface 21 there is a cartilage contacting surface 19.

The implant may be specially designed, depending on the appearance of the knee and the shape of the damage and in order to resemble the body's own parts, having a surface which preferably corresponds to a three dimensional (3D) image of a simulated healthy cartilage surface. The implant can thus be tailor-made to fit each patient's damaged part of the joint. Alternatively, the implant to may be of standard shapes and sizes.

Implant Body

The implant body 27 is in one embodiment substantially plate shaped, meaning that the shortest distance (represented by 24 in FIG. 3a) crossing the surface 15 of the implant body 27 is substantially larger, e.g. at least 1.5 times larger than the thickness 14 of the implant body 27. By substantially plate shaped is meant that the implant body 27 may be substantially flat or may have some curvature, preferably a 3D curvature of the articulate surface 15. The plate shaped implant body 27 has a cross-section 81 that substantially corresponds to the area of the damaged cartilage, see FIGS. 3c-f and 13a-l implant 10, with four exemplifying cross-sectional views, 81a-d. The articulate surface 15 of the plate shaped implant body 27 may have a curvature that substantially corresponds to the curvature of a healthy articulating surface at the site of diseased cartilage. The curvature may for instance correspond to a simulated healthy cartilage reconstructed from an image taken with MRI image or the CT-scanning of the damaged cartilage surface of the joint. Once the implant 10 is placed in the joint there will be a surface with no parts of the implant pointing up from or down below the surrounding cartilage—the implant is incorporated to give a smooth surface.

The size and the shape of the implant body 27 may be individually adapted, or may be chosen from a set of standards, dependent on the size of cartilage damage and location of the cartilage damage. The area and shape of the implant can be decided by the surgeon himself or be chosen from predetermined shapes. For instance the cross-section of the implant body 27 may have a circular or roughly circular, oval, triangular, square or irregular shape, preferably a shape without sharp edges (see e.g. FIGS. 3c-f and 13a-l, implant 10). The size of the implant 10 may also vary. The area of the articulate surface 15 of the implant varies in different realizations between 0.5 cm$^2$ and 20 cm$^2$, between 0.5 cm$^2$ and 15 cm$^2$, between 0.5 cm$^2$ and 10 cm$^2$, between 1 cm$^2$ and 5 cm$^2$ or preferably between about 0.5 cm$^2$ and 5 cm$^2$.

In general, small implants are preferred since they have a smaller impact on the joint at the site of incision and are also more easily implanted using arthroscopy or smaller open surgical procedures. The primary factor for determining the size of the implant is however the nature of the lesion to be repaired.

The articulate surface 15 of the implant body 27, and the core of the implant body 27, comprises a biocompatible metal, metal alloy or ceramic. More specifically it can comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia. Preferably the articulate surface 15 comprises a cobalt chrome alloy (CoCr) or stainless steel, diamond-like carbon or a ceramic. The articulate surface 15 and the core of the implant body 27 may comprise the same or different materials.

The articulate surface 15 may also be further surface treated in order to e.g. achieve an even more durable surface or a surface with a lower friction coefficient. Such treatments may include, for example, polishing, heat treatment, precipitation hardening or depositing a suitable surface coating.

The Bone Contact Surface

The implant body 27 has a bone contact surface (bone contact surface) 21, configured to face or contact the bone structure of the joint. In one embodiment the bone contact surface 21 comprises a biocompatible metal, metal alloy or ceramic, such as any of the metals, metal alloys or ceramic described above for the articulate surface 15. Preferably the bone contact surface 21 comprises a cobalt chrome alloy (CoCr), a titanium alloy, titanium or stainless steel.

In one embodiment the bone contact surface 21 comprises, or in one specific embodiment is coated with, a bioactive material. In an alternative embodiment, the bone contact surface does not comprise a bioactive material and/or is uncoated.

The bioactive material of the bone contact surface, if present, preferably stimulates bone to grow into or onto the implant surface. Several bioactive materials that have a stimulating effect on bone growth are known and have been used to promote adherence between implants and bone. Examples of such prior art bioactive materials include bioactive glass, bioactive ceramics and biomolecules such as collagens, fibronectin, osteonectin and various growth factors. A commonly used bioactive material in the field of implant technology is the bioactive ceramic hydroxyapatite (HA), chemical formula $Ca_{10}(PO_4)_6(OH)_2$. HA is the major mineral constituent of bone and is able to slowly bond with bone in vivo. HA coatings have been developed for medical implants to promote bone attachment. Another bioactive material commonly used in prior art is bioactive glass. Bioactive glasses, generally comprising $SiO_2$, $CaSiO_3$, $P_2O_5$, $Na_2O$ and/or CaO and possibly other metal oxides or fluorides, are able to stimulate bone growth faster than HA.

The bioactive materials described above have an anabolic effect on the bone i.e. stimulates bone growth. The fixation of the implant can also be improved by decreasing the catabolic processes i.e. decrease the amount of bone resorption next to the implant. The bone contact surface 21 and/or the extending post can also be modified with bisphosphonates. Bisphosphonates are substances that decrease the catabolic process of bone and binds readily to HA. One way to bind the bisphosphonate to the surface is by coating it with HA, which it readily binds to. The implant can also simply be immersed in a bisphosphonate solution or linked with some other biocompatible molecule e.g. carbodiimides, N-hydroxysuccinimide (NHS)-esters, fibrinogen, collagen etc.

In one embodiment the bone contact surface 21 is coated with a double coating. Such double coating may for instance comprise an inner coating comprising titanium (Ti). The second, outer coating, that is configured to contact the cartilage and or bone, is preferably a hydroxyapatite and/or beta tricalcium phosphate (TCP) coating containing more than 95% hydroxyl apatite or 95-99.5% hydroxyapatite. By this design even more long-term fixation of the implant is achieved, since bone in- or on-growth to the implant is further stimulated by the titanium, even if the more brittle hyroxyapatite would eventually shed/dissolve.

The bone contact surface may also be further modified with fluoro compounds or acid etching to enhance the bioactivity and the osseointegration of the surface. Another method to facilitate osseointegration is blasting of the bone contact surface.

The Extending Post

The implant replaces an area of damaged cartilage in an articulating surface of a joint. Before the implant is placed in the desired position, the damaged cartilage is removed and also a part of the bone beneath. Furthermore, a hole can be drilled to fit the implant structure. An extending post or rod-part 23 of the implant 10 (see FIGS. 3a-b), may be used for securing the implant 10 in the drilled hole of the bone. The length of the extending post 23, extending from the bone contact surface 21, is adjusted to a length needed to secure the implant 10 in the bone. The extending post 23 is intended to give a primary fixation of the implant 10; it provides mechanical attachment of the implant 10 to the bone in immediate connection with the surgical operation.

The position of the extending post 23 on the bone contact surface 21 can be anywhere on the bone contact surface 21 or the extending post 23 may have a central position.

The extending post 23 has a physical structure in the form of for example a cylinder or other shapes such as one or more of a small screw, peg, keel, barb or the like.

The extending post 23 can in one embodiment be coated with a bioactive material, for example a bone stimulating material with single or double coatings and/or, a substance inhibiting bone resorption such as described for the bone contact surface 21 above. The surface of the extending post can also be further modified using e.g. fluoro compounds or acid etching or blasting, to enhance osseointegration of the surface.

In another embodiment, the extending post 23 is uncoated and the extending post may comprise e.g. a metal, metal alloy or ceramic material, such as the metal, metal alloys or ceramic materials described for the articulate surface 15 above.

In one embodiment, as exemplified in FIGS. 3a-b, the extending post 23 has a positioning part 25, where the positioning part 25 is located distal to the plate shaped implant body 27. The longitudinal symmetry axes of the first part of the extending post 23 and the positioning part 25 coincide. The diameter of the positioning part 25 is smaller than the diameter of the first part of the extending post 23.

Grafted Plug or Artificial Plug

In an alternative embodiment the surgical kit of the present disclosure may be used for mosaicplasty or osteochondral autograft transfer (OATS). In such case the implant to be used with the surgical kit does not have a plate shaped implant body with extending post, but rather is a grafted plug taken from healthy bone and cartilage, see FIGS. 4a-b, or an artificial plug, having the same general shape as a grafted plug but being made of an artificial material (see below). FIG. 4a shows a grafted plug 600 in the form of a bone and cartilage plug, such as a osteochondral plug, that has been harvested from a nonbearing part of a joint. The implant body 627 of the grafted plug 600 has a cylindrical to a substantially cylindrical form. By cylindrical to a substantially cylindrical form is meant a form or shape having parallel side walls, and having a cross-sectional profile 81 that is preferably circular or roughly circular but that may also have any other shape, including oval, triangular, square or irregular shape, preferably a shape without sharp edges, see exemplifying cross-sections 81a-d in FIGS. 4c-f. At the upper part of the grafted plug 600 there is healthy cartilage 606 from the site of harvest, while the lower portion of the grafted plug 600 comprises bone tissue.

The grafted plug 600 may be further reshaped after harvesting by using a sharpener tool, see FIG. 4b. The sharpener tool may be constructed as a pencil sharpener, with a sharp blade, but which may be used to adjust the shape and/or the length of the bone part of the grafted plug 600, in order to arrange such that several plugs may fit together in an area of cartilage damage. The implant body 627, i.e. the upper part of the sharpened grafted plug 600, still has a cylindrical form, as defined above, i.e. with parallel side walls and a cross-sectional profile 81 that can have various shapes.

In another embodiment the plug used for mosaicplasty or OATS may be an artificial plug made of an artificial material such as synthetic polymer scaffolds, e.g. polylactide-co-glycolid, calcium sulfate, polycarbonate polyurethane or polyglycolide fibers or synthetic calcium. Such artificial plugs have the same geometrical shapes as the grafted plug 600 described above. Importantly for the present disclosure the artificial plug, like grafted plug 600, has an implant body 627 with a cylindrical form, that is a form or shape with parallel side walls and with a cross-sectional profile 81 that is preferably circular or roughly circular, but that may also have any other shape, including oval, triangular, square or irregular shape, preferably a shape without sharp edges.

An grafted plug 600 or an artificial plug has a cross-sectional area that is between 0.5 $cm^2$ and 5 $cm^2$, between 0.5 $cm^2$ and 3 $cm^2$, or preferably between about 0.5 $cm^2$ and 2 $cm^2$ at its cylindrical portion. It has a length 710 that is between 1 and 4 cm, or between 1.5 and 3 cm. The cross-sectional diameter at the cylindrical portion may for example be 0.1-1 cm.

FIGS. 4g-h show a cartilage damage site repaired using mosaic repair technique, FIG. 4g from a cross-sectional side view of the joint, and FIG. 4h from above. Several grafted plugs 600 have been inserted at the site of damaged or diseased cartilage, to form a mosaic pattern. FIG. 4h also shows that grafted plugs 600 have been harvested from the healthy part of the joint (right hand side of the figure).

According to an embodiment, the amounts of plugs and also the size and shape of the healthy cartilage and bone plugs are selected depending on the shape and size of the injury.

The Set of Tools

The set of tools comprises a guide base 12, to which a guide body 13 with a guide channel 54 is releasably attached, see FIGS. 5a-7. It may also comprise a selection of insert tools, for use when mounting an implant 10, a grafted plug 600 or an artificial plug to the implant site, see FIGS. 2 and 8-11b. The insert tools are in operation inserted in the guide channel 54 of the guide body 13 and fits in the guide channel 54, with a slight tolerance to allow a sliding movement of the insert tool in the guide channel 54. The cross-sectional profile, and thus the circumferential shape of the insert tools, corresponds to the chosen cross-section 81 of the implant body 27, 627 of the implant 10, grafted plug 600 or artificial plug, in size and shape (see FIGS. 13a-l). The insert tools are in different embodiments provided in the form of for example a cartilage cutting tool, a punch, a drill, a drill guide, a bone cutting tool, a reamer guide and/or a hammer tool. Some insert tools are used together with further tools such as a drill bit and/or a reamer bit. An exemplifying set of insert tools will be described herein. The modular surgical kit may further be used with other insert tools, such as insert tools disclosed in PCT application PCT/EP2011/058473 or European patent application 11163405.1.

Guide Base, Guide Body and Guide Insert

Figure 5A:
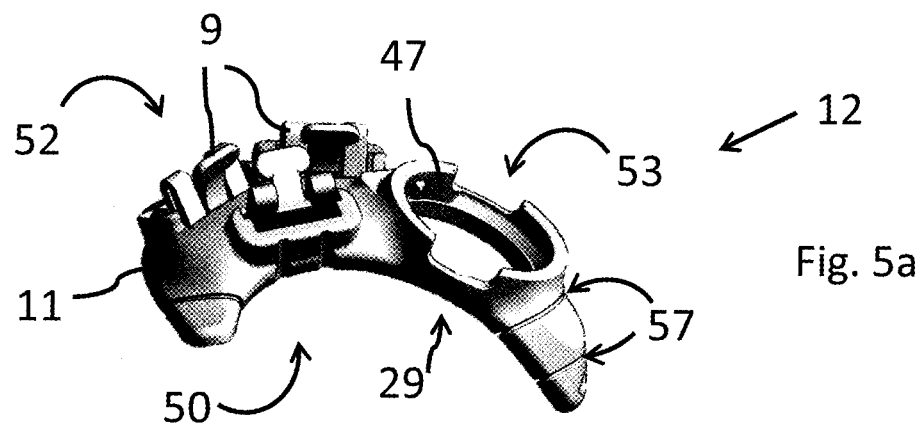
FIG. 5a-d show exemplifying embodiments of a guide base, for use in a knee joint (a-b) and in a toe joint (c-d) respectively.
Figure 5B:
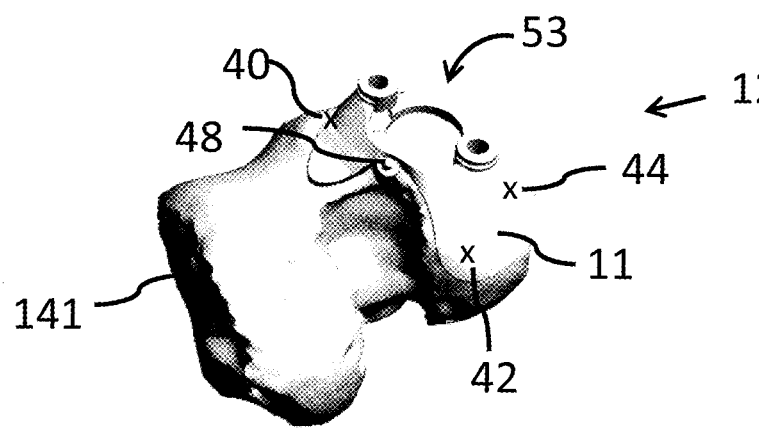
Figure 5C:
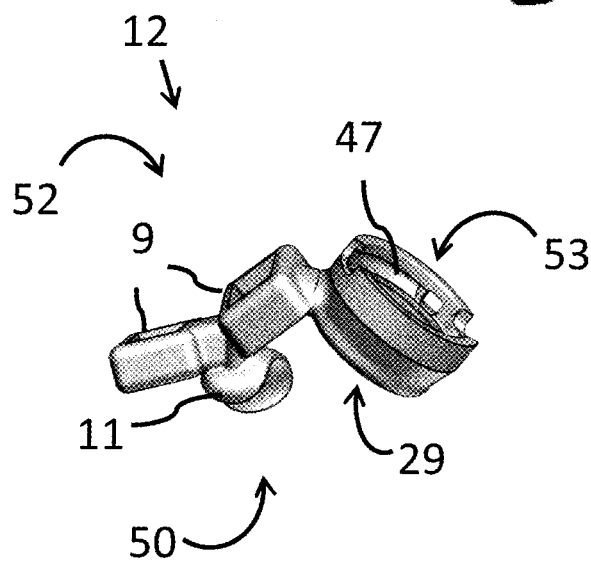
Figure 5D:
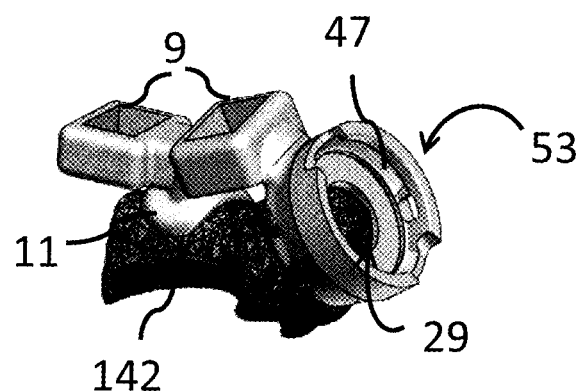
Figure 6:
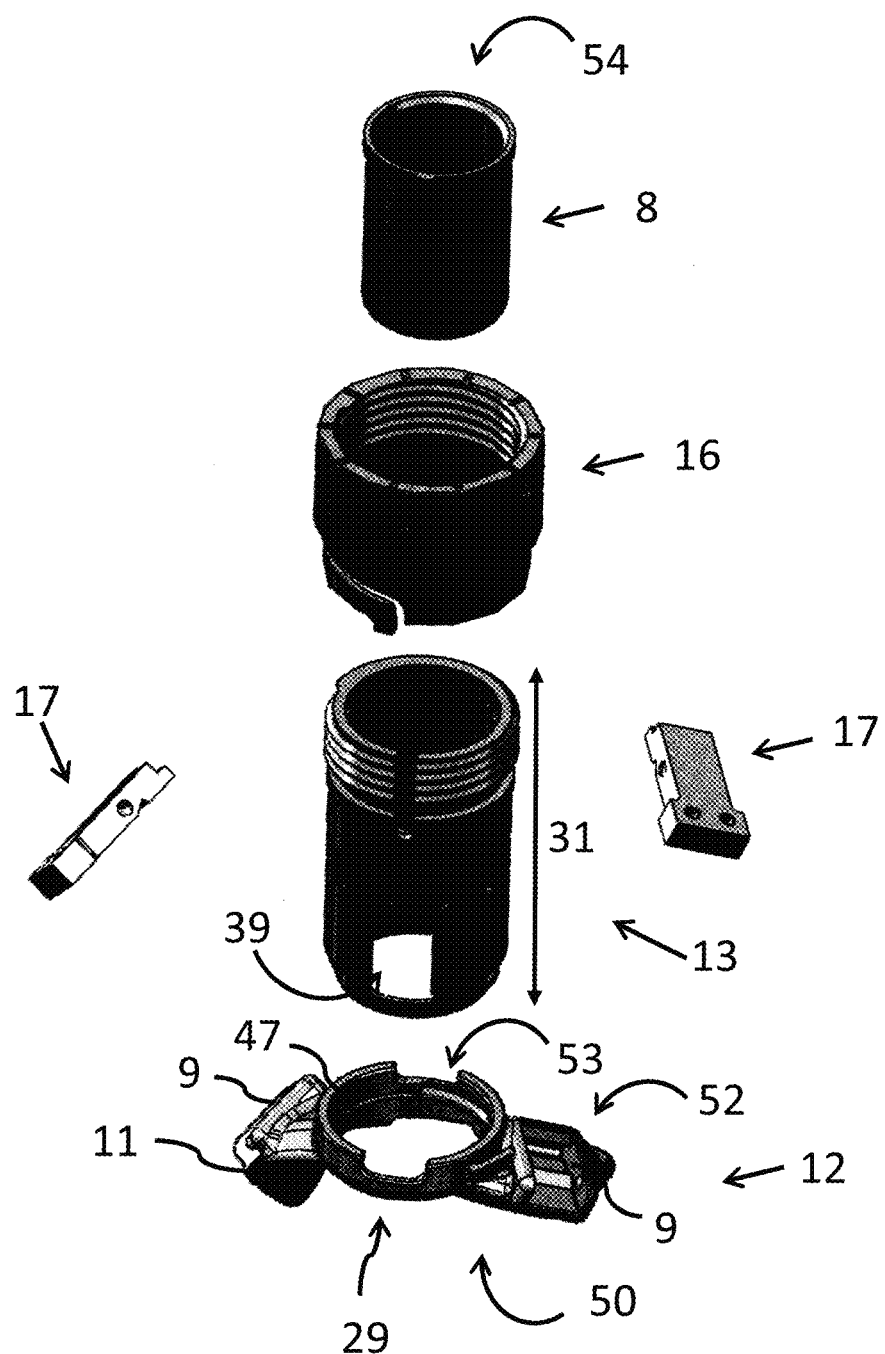
FIG. 6 shows an exemplifying embodiment of a modular surgical kit, fur use in a knee joint.
Figure 7:
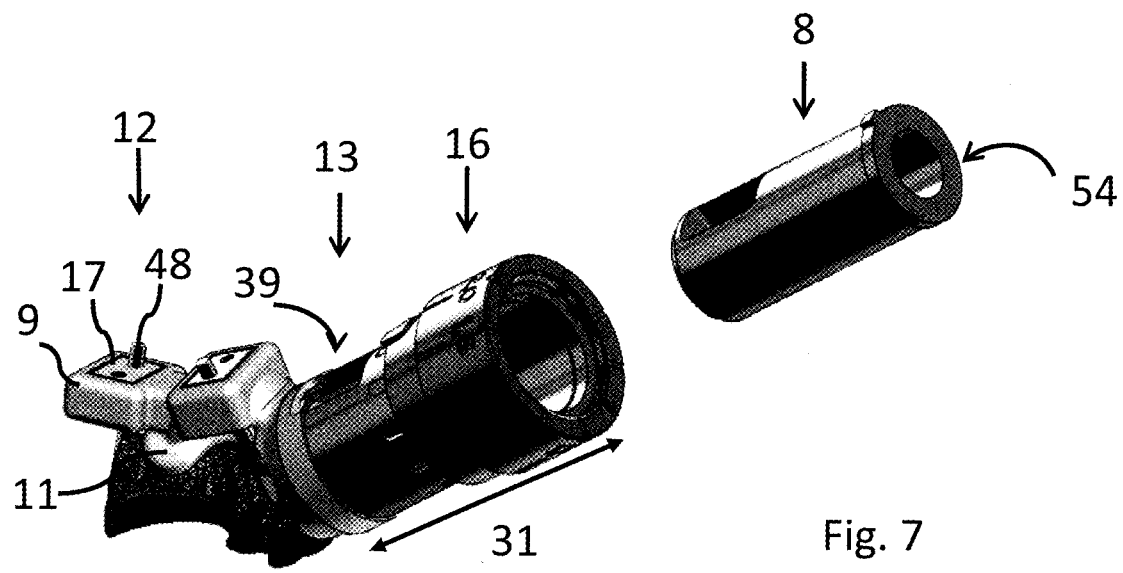
FIG. 7 shows an exemplifying embodiment of a modular surgical kit, fur use in a toe joint.

FIG. 6 shows an exemplifying embodiment of a modular surgical kit of the disclosure, for use in a knee joint. FIG. 7 shows an exemplifying embodiment of a modular surgical kit, for use in a toe joint. The modular surgical kit comprises a guide base 12 that is releasably attached to a guide body 13. FIGS. 5a-d show the guide base 12 in more detail.

Two embodiments of a guide base 12 for use in a knee joint are shown in FIGS. 5a-b, and one embodiment of a guide base 12 for use in a toe joint is shown in FIGS. 5c-d. In FIGS. 5b and 5d the guide base 12 is placed on the femoral bone 141 of the knee joint and a falangeal joint bone 142 of a toe respectively. The guide base 12 comprises a positioning body 11 and a guide hole 53, which may alternatively be denoted guide recess or guide opening or similar, through said positioning body 11. The positioning body 11 has a cartilage contact surface 50 that has a shape and contour that is designed to correspond to and to fit the contour of the cartilage or the subchondral bone in the joint in a predetermined area surrounding the site of diseased cartilage. The cartilage contact surface 50 may be adapted to fit to the joint of an average patient or may be adapted, i.e. custom made, for an individual patient. The positioning body 11 also has a top surface 52 facing the opposite direction compared to the cartilage contacting surface 50.

The guide hole 53 has a muzzle 29 on the cartilage contact surface 50, at a position of the positioning body 11 that corresponds to the site of the diseased cartilage, i.e. the site of implantation. In one embodiment the guide hole 53 has a cross-sectional profile that is designed to correspond to the cross-section 81 of the implant body 27, 627 of the implant 10, grafted plug 600 or artificial plug to be implanted. In another embodiment the guide hole 53 has a cross-section that is slightly larger than the cross-section 81 of the implant body 27, 627. In a further embodiment the cross-sectional profile of the guide hole 53 need not correspond to the cross-section 81 of the implant body 27, 627. Where the cross-sectional profile of the guide hole 53 is different from the cross-section 81 of the implant body 27, 627, correspondence or matching to the cross-section 81 of the implant body 27, 627 is provided by the cross-sectional profile of the guide channel 54 of the guide body 13 only (see below).

An embodiment of a guide body 13 is shown in FIGS. 6 and 7. The guide body 13 has a guide channel 54 that extends through the guide body 13. The outer shape and design of the guide body 13 may vary, as is schematically illustrated by a circular design 13a and a square design 13b in FIGS. 13a-c (implant 10 and guide body 13a, 13b seen from above). The guide channel 54 of the guide body 13, however, has an inner cross-sectional profile (see FIG. 13a-l) that is designed to correspond to the cross-section 81 of the implant body 27, 627. In other words, the implant body 27, 627 fits the guide channel 54, with a slight tolerance to allow a sliding movement of the implant in the guide channel 54.

In an alternative embodiment the guide body 13 has a guide channel that has a cross-sectional profile which is larger than the cross-sectional profile 81 of the implant body 27, 627. In this case the guide channel 54 that is designed to correspond to the cross-section 81 of the implant body 27, 627 is instead provided by a guide insert 8 (see FIGS. 6 and 7, and top view in FIG. 13a-l). The guide insert 8 is designed to have outer proportions to make it fit in the guide channel of the guide body 13. Its guide channel 54 is designed to have an inner cross-sectional profile that corresponds to the cross-section 81 of the implant body 27, 627. In other words, the implant body 27, 627 fits the guide channel 54, with a slight tolerance to allow a sliding movement of the implant in the guide channel 54. In this way the guide insert 8 works as an adapter, such that a guide body 13 with a guide channel of a certain size might be used for implantation of implants of various sizes, by use of guide inserts 8 with varying guide channels 54 that fit implants of corresponding varying sizes.

The height 31 of the guide channel 54 must be sufficiently long to give support to the tools used inside the guide body 13. The height 31 of the guide channel 54 is preferably also sufficiently high to be easily accessible for the surgeon during surgery. In one embodiment, the top of the guide channel 54 is designed to project above the tissue surrounding the surgery cut when the guide tool is placed on the cartilage in a joint during surgery. The height 31 is preferably higher than the thickness of the surrounding tissue. In this way, the opening of the guide channel 54 is easy to access for the surgeon. The height 31 of the guide channel 54 is between 1 and 10 cm, preferably 3-10 cm and always sufficiently high to ensure stabilization of the tools that are to be inserted into the guide channel 54.

Figure 8:
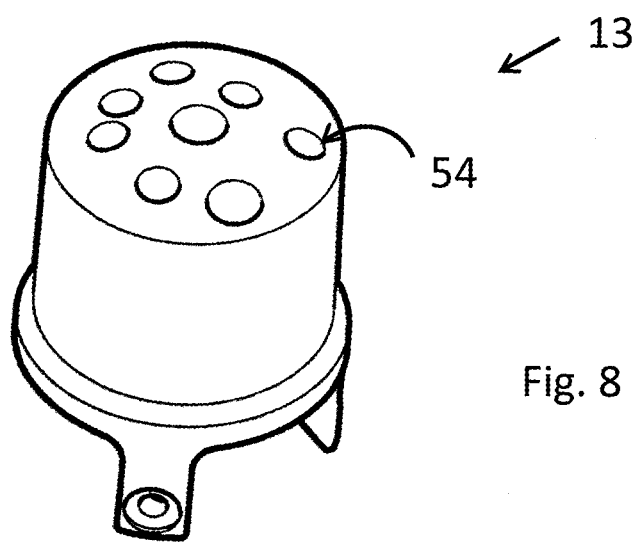
FIG. 8 shows an exemplifying embodiment of a guide body, for use in mosaicplasty surgery.

FIG. 8 shows an embodiment of a guide body 13, for use in mosaicplasty or OATS surgery. The guide body 13 comprises at least two guide channels 54. Each of the guide channels 54 is designed to have a cross-sectional profile that corresponds the cross-section 81 of an implant body 627 of a grafted plug 600 or an artificial plug. The at least two guide channels 54 may have cross-sectional profiles that are identical. Alternatively their cross-sectional profiles may be different in shape and/or size/area, depending on the cross-sectional profile 81 of the respective grafted plugs 600 or artificial plugs, that are to be implanted. Each of the guide channels 54 may also be arranged in the guide body 13 at different angles, depending on the angle in which the respective plugs are to be implanted.

The guide body 13 may be provided with an inspection window 39, i.e. a window or hole through the side of the guide body 13, into the guide channel 54, see FIGS. 6 and 7. The inspection window 39 facilitates inspection of the site of implantation during surgery, also when the guide body 13 is attached to the guide base 12, see FIGS. 14c-h.

The guide base 12 comprises means for releasable attachment 47 to the guide body 13, see FIGS. 5a and b-c and FIG. 6. Such means 47 is arranged such that when the guide body 13 is attached to the guide base 12 the guide body 13 extends from the top surface 52 of the guide base 12. Such means for releasable attachment 47 is also arranged such that, when attached, the guide channel 54 is positioned in relation to the positioning body 11 such that its muzzle 32 emanates at a site corresponding to the site of implantation into the bone, which is also at the site of the guide hole 53. The angle of the guide hole 53 in the positioning body 11 and the arrangement of the releasable attachment means 47 also determine the angle of the guide channel(s) 54 in relation to the positioning body 11 and implantation site. The guide hole 53 and/or the means for releasable attachment 47 are arranged such that, when the guide body 13 is attached to the guide base 12, the angle of the guide channel(s) 54 will correspond to the angle in which the implant 10, grafted plug(s) 600 or artificial plug(s) is/are to be inserted. For small implants 10 the angle of implantation, and thus of the guide channel 54, is most often perpendicular to a tangential plane of the site of implantation. For implants 600 used in mosaicplasty or OATS surgery the angle of implantation of the respective plugs, and thus of the respective guide channels 54, may vary.

In one embodiment the cross-sectional profile of the guide hole 53 and the guide channel 54 correspond and the guide hole 53 and the guide channel 54 are aligned. That is, the symmetry axis of the guide hole 53 and the longitudinal symmetry axis of the guide channel 54 approximately coincide. The cross-sectional profile of the guide hole 53 and of the guide channel 54 may in another embodiment be different. The cross-section of the guide hole 53 must however be at least as big as the cross-section of the guide channel 54, the cross-section of the guide channel 54 must correspond to the cross-section 81 of the implant body 27, 627 and the muzzle 32 of the guide channel 54 must emanate at a site corresponding to the site of implantation, when the guide body 13 is attached to the guide base 12.

The means for releasable attachment 47 may be provided by a snap fit function between the guide base 12 and the guide body 13, and/or by the guide hole 53, or part of the guide hole 53, and the lower part of the guide body 13 being provided with matching threads and/or bayonet mount and/or other form fitting mechanisms. Other releasable attachment mechanisms are however also conceivable.

The guide base 12 is easy to place due to the precise fit of the positioning body 11 on the cartilage surface. The guide base 12 is designed to be inserted in a lesion which is as small as possible to be able to repair the specific cartilage damage. The size and shape of cartilage contact surface 50 of the guide base 12 is determined depending on the size and shape of the damaged cartilage and also depending on the position of the cartilage damage in the joint. The size and shape of the surface 50 and the positioning body 12 is a consideration between the following aspects; minimize surgery lesion, maximize stability for the guide base 12, anatomic limitations on the site of the injury, and that not all cartilage surfaces in a joint can be used for placement of the guide tool. A large spread of the cartilage contact surface 50 is to prefer to get good stability of the guide tool, however, a large surface area of the surface 50 may also lead to a large surgical intervention and this is undesired. Thus the size of the cartilage contact surface 50 and of the positioning body 11 is determined by a balance between the desire to achieve good positioning stability and small surgical operations. Also, the cartilage contact surface 50 does not need to have a continuous, regular shape, but may have an irregular shape, as long as it gives adequate support and stable positioning of the guide base 12.

When designing the guide tool, the cartilage contact surface 50 can be designed to cover three points (see FIG. 5b, points 40, 42, 44 for an example) distributed over the cartilage surface of the joint where the implant is to be inserted. The points are chosen to give maximum support and positional stability for the positioning body 11 and thus these points, either decided and identified by the surgeon or automatically identified by design software, serve as the ground when designing the surface 50 of the guide base 12. The cartilage contact surface 50 can also be formed such that it uses the curvature in the cartilage surface in a joint for stability. For example, in a knee joint, the condyles are separated from each other by a shallow depression, the posterior intercondyloid fossa, this curvature together with the medial epicondyle surface can be used to give the cartilage contact surface 50 a stabile attachment to the cartilage surface in a knee joint. The surface is in one embodiment a continuous surface covering a selected area surrounding the cartilage damage. In another embodiment the cartilage contact surface is distributed over a plurality of points, preferably three or more of separated contact points. The cartilage contact surface does not need to be a continuous, regular surface, but preferably has at least three points exemplified by 40, 42 and 44 for stability.

Optionally the cartilage contacting surface 50 can be further stabilized by attachment with nails, rivets or similar attachment means 48 to the bone surrounding the cartilage in a joint (see FIG. 5b). This additional attachment with rivets or the like gives additional support and stability and also gives the possibility to keep the cartilage contact surface as small as possible. The position of the rivets may be predetermined and marked out on the surface 50 by premade drill holes.

In an alternative embodiment the positioning body 11 may be arranged with attachment means 9 for attachment of adaptors 17, pins and possibly other devices to the guide base 12, see FIGS. 5a, c and d, 6, 7 and 14a-b. Such attachment means 9 may for example connect to the adaptor 17, pin or other device through a snap fit function, thread function or any other form fitting function. The adaptors 17 shown in FIGS. 6, 7 and 14b have holes or bores that can receive pins, nails, rivets or similar means 48 in order to secure the attachment of the guide base 12 to the bone as described above. The elongated form of the adapters 17 allow such pins or similar means to be inserted into the bone at a distance from the site of implantation. Adaptors of the embodiment shown in FIG. 14b also have a shape, i.e. both bent and somewhat elongated, such that the pin holes will be both lifted or elevated from the joint surface and situated at a distance from the site of implantation. This shape is advantageous since it will be easier to keep the surface of the joint free of waste and debris from the implantation wound and surroundings and since it will be possible to insert the pins more straight from above. Inserting the pins from at an angle from the side often means than the skin around the site of incision has to be more split open and thus that the wound will be bigger. This is thus avoided when using adaptors as seen in FIG. 14b.

As stated above, the size and shape of the positioning body 11 of the guide base 12 is determined in order to minimize the surgical intervention while also maximizing the stability of the guide base 12 in the joint. While designing the guide base 12, e.g. by use of X-ray, MR or CT images from the patient it is normally desired to have a positioning body that is as large as possible, in order to ensure maximum stability and proper positioning of the guide base 12 in the joint. However, not all facts on the patient's joint may be known through the X-ray, MR or CT images, and thus the surgeon may want to adjust the positioning body 11 during surgery. For example, osteophytes might have formed in the joint and are often difficult to identify in the imaging procedures. Also, the surgeon might find during surgery that the shape of the guide base 12 requires an unnecessarily large incision to be able to insert the guide base 12 into the joint. In order to facilitate adaptation of the size and shape of the guide base 12 during surgery, the positioning body may be arranged with breakage means 57 that enable easy removal of part(s) of the positioning body 11 by tearing, fracturing or similar ways of breakage, see e.g. FIG. 5a. Such breakage means 57 may for example be provided through grooves, slots or perforations or other weakening of the structure.

The guide base 12 with guide body 13 aid with exact precision removal of a volume of cartilage and subchondral bone and also guide the placement of the implant 10, the grafted plug 600 or the artificial plug in for example a knee. Placement of the guide base 12 on the cartilage surface of a knee or a toe can be seen in FIGS. 5b and 5d. The use of the guide base 12 and guide body 13 is further explained below in connection to FIGS. 14a-t.

The guide base 12 and the guide body 13 are manufactured using suitable materials that are approved for use in medical procedures, e. g. a ceramic, plastic, metal, metal alloy or alumina material, or a combination. The guide base 12, especially the cartilage contact surface 50, is also preferably made of a material that is smooth, even and/or has low friction, in order to lessen the risk of wear and damage to the cartilage on which it is to be placed. Such materials include e.g. metals ceramics and polymers such as acrylonitrile butadiene styrene (ABS). The used materials may further be polished. In a preferred embodiment the guide base 12 is made of a plastic material, such as polyamide or epoxy, while the guide body 13 is made of a metal material or stainless steel. The plastic material of the guide base 12 is easy to manufacture, e.g. using selective laser sintering (SLS) or stereolithography (SLA) technologies, also when adapted for a specific patient. It is also gentle to the cartilage surface of the joint. The metallic material of the guide body 13 on the other hand, provides a wear resistant material that is to be in contact with the insert tools, thus minimizing the risk of generating wear debris from the guide body for example during drilling. It is also autoclavable and thus reusable. In one embodiment the guide base 12 is adapted to a specific patient, by having a cartilage contact surface 50 and a positioning body 11 that are designed to match the cartilage surface and the shape of the joint of the patient. In one embodiment the guide body 13 is made in a number of standard shapes and sizes, matching corresponding shapes and sizes of a set of standard implants 10, while in another embodiment the guide body 13, as well as the implant 10, is also adapted to the specific patient.

Drill Adjustment Device

In a preferred embodiment the surgical kit further comprises a drill adjustment device 16 as for example illustrated in FIGS. 2, 6 and 7. The drill adjustment device 16 of the embodiment shown is arranged for attachment to the top of the guide body 13, e.g. by threads. The drill adjustment device 16 is further arranged such that it may be used to adjust the length of the guide channel 54. The length 31 of the guide channel 54 determines the depth of drilling and cutting of the bone in the joint, as will be described further below. Thus, by being able to adjust the length 31 of the guide channel the surgeon is also able to adjust the depth of drilling and cutting into the bone. The length 31 of the guide channel may be varied since the guide body 13 and the drill adjustment device 16 are able to move in relation to one another when attached. This may for example be achieved by corresponding threading of the guide body 13 and drill adjustment device. Further, the guide body 13 and/or drill adjustment device may be arranged such that the length 31 of the guide channel may be varied at certain intervals, e.g. at 200 μm intervals, or any other desired interval. This may for instance be achieved by arranging the guide body 13 and/or the drill adjustment device 16 such that they are able to move in relation to one another at certain intervals. For example, the threading may be arranged such that the guide body 13 and drill adjustment device 16 may be turned in relation to one another at preset intervals, and that they are locked in relation to each other or prone to hook each other at those intervals. This is readily implemented by a snap fit function.

The drill adjustment device 16 may be used by the surgeon to adjust the depth of drilling, e.g. by increasing the drill depth in steps at the preset intervals. The drill adjustment device is advantageously used together with an implant dummy 36, as described below, to make sure that the drill depth in the bone matches the height 14 of the implant body 27. This ensures that the articulate surface 15 of the implant 10 will be in line with the surrounding cartilage at the site of implantation once implanted. For further description of how the drill adjustment device 16 is used during surgery, see below in connection with FIGS. 14j-p.

An alternative embodiment of a drill depth adjustment tool is disclosed in PCT application PCT/EP2011/058473, see e.g. pages 20-21 of the description and FIGS. 12-14. Another way to adjust the drill depth is also to have an adjustable depth gauge on the drilling tool, see below.

Cartilage Cutting Tool

Figure 9:
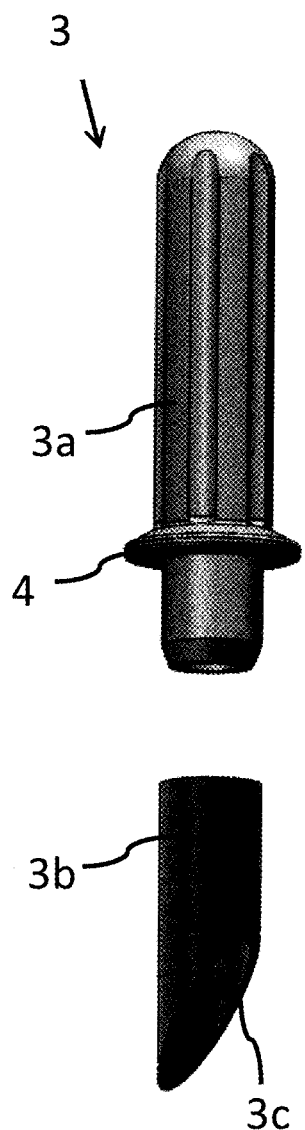
FIG. 9 shows an exemplifying embodiment of a cartilage cutter.

The cartilage cutting tool 3 is a tool which is used to cut the cartilage in the joint around the area of damaged cartilage to prepare for the insertion of the implant. The cartilage cutting tool may for example be a cartilage cutter 3, as shown in FIGS. 2 and 9, a punch or a cartilage cut drill. It is used inside the guide channel 54 of the guide body 13 and fits in the guide channel 54, with a slight tolerance to allow a sliding movement of the cartilage cutting tool 3 in the guide channel 54 (see FIG. 13a-l). The cartilage cutting tool 3 preferably cuts the cartilage so that the cut edges of the cartilage are sharp and smooth. These sharp and smooth edges are of great importance when the implant is placed into the prepared recess in the cartilage and bone. A hole in the cartilage which is cut (or punched or drilled) with the cartilage cutting tool 3 according to the disclosure ends up with a precise fit of the implant into the prepared cartilage since the cartilage cutting tool allows for an exact, precise cut. The recess in the cartilage, made by the cartilage cutting tool 3 always corresponds to the chosen cross-section 81 of the implant body 27 in size and shape.

In one exemplifying embodiment, the cartilage cutting tool is a cartilage cutter 3. The cartilage cutter 3 is used to cut the cartilage in the joint around the area of damaged cartilage to prepare for the insertion of the implant with a cutting technique.

The cartilage cutter 3 has a handle 3a, a cartilage cutter body 3b and a cutting blade with sharp cutting edges 3c. The cartilage cutter body 3b has a cross-sectional profile that is designed to correspond to the inner cross-sectional profile of the guide channel 54 with a tolerance enabling the cartilage cutter body 3b to slide within the guide channel 54 (see FIG. 13a-l). Also, the cross-sectional profile is designed to correspond to the cross-section of the implant. Thus, the cartilage cutter body 3b fits the inside of the guide channel 54, see FIG. 13, with a slight tolerance to allow a sliding movement of the cartilage cutter in the guide channel 54. The fit ensures the correct, desired placement of the cartilage cutting edges 3c on the cartilage surface and thus the precise removal of the damaged cartilage area.

The cartilage cutter 3 of the embodiment shown in FIG. 9 has a cartilage cutter body 3b comprising a circular cutting blade that has been cut at an angle that is not perpendicular to the length of the cutter body 3b. This creates an oval cutting edge 3c with a pointy appearance, further increasing the sharpness of the cartilage cutter 3. The cutting edge 3c is arranged to cut the cartilage in a shape corresponding to the cross-sectional profile 81 of the implant body 27.

The material of the cartilage cutter body 3b is chosen from materials which can give the cartilage cutter 3 sharp cutting edges 3c. The material also needs to be stable in order to withstand the pressure when the cartilage cutter 3 is pushed into the cartilage. Examples of such materials are metals such as stainless steel or ceramic material or a plastic material or a hard coated material, preferably stainless steel.

The cutter body 3b may be permanently attached to the handle 3a, or may, more preferably, be removably attached to the handle 3*a*, such that the handle 3*a* is reusable while the cutter body 3*b* is be exchangeable (see FIG. 9).

The cartilage cutter 3 may be provided with a safety stop 4. The safety stop 4 has a cross-sectional profile that is larger than the gross sectional profile of the guide channel 54. In case the cutter would risk digging too deep into the bone the safety stop 4 will be stopped against the top of the guide body 13 and/or drill adjustment device 16, thus preventing the cartilage cutter 3 to be pushed deeper into the bone. This could happen e.g. when the patient suffers from osteoporosis. The distance between the tip of the cutting edge 3*c* and the safety stop 4, and the relation between that distance and the length 31 of the guide channel 54, will determine the depth that the cartilage cutter 3 is allowed to go into the cartilage and/or bone. The safety stop 4 may be arranged such that that distance is adjustable.

In alternative exemplifying embodiments, the surgical kit may comprise a cartilage cutting tool in form of a punch, to punch out the cartilage, or in form of a cartilage cut drill, to cut the cartilage and also cut/carve/drill the underlying bone, as are disclosed in PCT application PCT/EP2011/058473, see pages 17-18 and FIGS. 2, 5*a-b* and 10. The punch may for instance be advantageous when the implant 10 has a non-circular shape and/or the extending post 23 is not centrally placed in relation to the implant body 27.

Drill and Bone Remover

Figure 10:
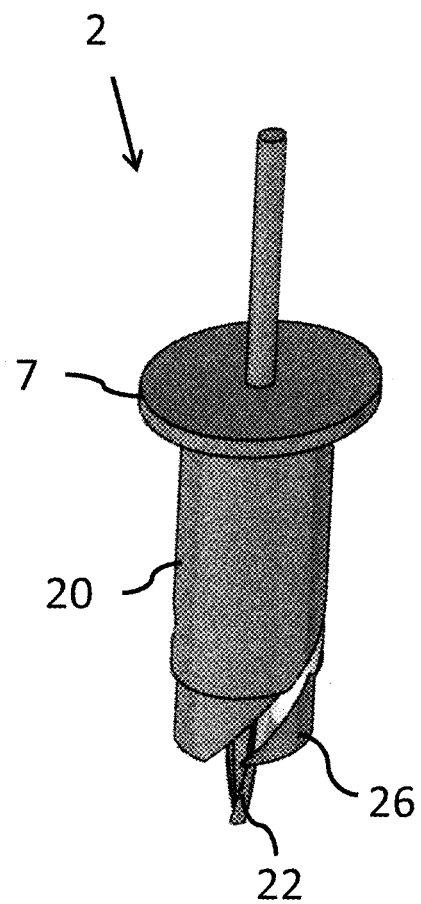
FIG. 10 shows an exemplifying embodiment of a drill and bone remover.

In one embodiment, the surgical kit comprises a drill and bone remover 2 (see FIGS. 2 and 10) that is used to drill a hole in the bone at the site of cartilage damage, for fastening of the extending post 23 of the implant 10 in the bone tissue, and simultaneously create a recess in the bone tissue at the site where the implant body 27 is to be received. The drill and bone remover 2 comprises a drill and bone remover body 20, a central drill 22 and a bone remover 26, as shown in FIG. 10. The central drill 22 extends from the center of the drill and bone remover body 20, i.e. corresponding to the position of a centrally placed extending post 23 on an implant 10 having a circular implant body 27. The diameter of the central drill 22 is the same as, or slightly smaller than, the diameter of the extending post 23 of the implant 10 that is to be implanted. The bone remover 26 has a cutting edge that is placed peripherally around the central drill 22. The diameter of the bone remover 26 is the same as, or slightly smaller than, the diameter of the implant body 27 of the implant 10 that is to be implanted, thus creating a recess that matches the implant body, in which the implant body can be received. The cutting edge of the bone remover 26 is hard enough for cutting or carving bone. It may be made of materials such as stainless steel.

The drill and bone remover body 20 is designed to fit the inside of the guide channel 54 of the guide body 13, with a slight tolerance to allow a sliding movement of the drill and bone remover 2 in the guide channel 54. In other words, the cross-sectional profile of the drill and bone remover body 20 matches the cross-sectional profile of the guide channel 54 as well as the of the implant 10, see FIGS. 13*a-l*. The fit ensures the correct, desired placement of the drill and bone remover 2 on the cartilage surface and thus ensures the precise direction and placement of the drill hole for the extending post 23, as well as the recess for the implant body 27, in the bone.

The drill and bone remover 2 is also equipped with a depth gauge 7. The depth gauge 7 of the drill and bone remover determines the depth of the created drill hole as well as the recess for the implant body 27. The depth gauge 7 has a cross-sectional profile that is larger than the cross sectional profile of the guide channel 54. The depth gauge 7 will, during the surgical procedure, rest against the top of the guide body 13 and/or drill adjustment device 16, thus preventing the drill and bone remover 2 to drill/carve/cut deeper into the bone. The distance between the tip of the cutting edge of the cutter 2 and the depth gauge 7, and the relation between that distance and the length 31 of the guide channel 54, will determine the depth that the is allowed to go into the cartilage and/or bone. The depth gauge 7 may be arranged such that that distance is adjustable. In a more preferred embodiment the distance is fixed and instead the drill/cut/carve depth is adjusted by adjusting the length 31 through the drill adjustment device 16.

See FIG. 14*g-p* for a demonstration of how the drill and bone remover 2 is used and how the drill depth is adjusted using the drill adjustment device 16.

In alternative exemplifying embodiments, the surgical kit may, instead of an integrated drill and bone remover, comprise a drill bit for drilling the hole for the extending post and a reamer for removing bone where the implant body is to be received in the bone. Such embodiments may also comprise a drill guide and/or a reamer guide. Examples have been disclosed in PCT application PCT/EP2011/058473, see pages 18-20 and 21 of the description and FIGS. 6-7. Such tools may for instance be used when the implant 10 has a non-circular shape and/or the extending post 23 is not centrally placed in relation to the implant body 27.

Implant Dummy and Dummy Reference

The implant dummy 36 and dummy reference 37, see FIGS. 2 and 11*a-b*, are used to make sure that the cut, carved or drilled recess in the bone that is to receive the implant body 27, is deep enough to fit the implant. This is very important, since the articulate surface 15 of the implant 10 must not project over the surface of the surrounding cartilage tissue. If it would it could cause a lot of damage to the surrounding cartilage and to the cartilage on the opposite side of the joint. Preferably the articulate surface 15 should form a continuous surface with the surrounding cartilage, neither projecting above nor being sunken below the surface of the surrounding cartilage. The checking of the recess depth is difficult or impossible to do with the implant 10 itself, since the implant 10, e.g. with its extending post 23, is designed to be fixed in the bone once inserted, and thus is difficult or impossible to remove. The implant dummy, on the other hand, is designed for easy removal from the recess once the recess depth has been checked.

The implant dummy 36, see FIG. 11*b*, has an implant element 41 that is designed to match the implant body 27. The lower surface 41*a* of the implant element 41 is a replica of the bone contact surface 21 of the implant that is to be implanted. That is, if the implant 10 and bone contact surface 21 is custom made for the specific patient, the implant element 41 and its lower surface 41*a* will also be custom made and the lower surface 41*a* be a replica of the bone contact surface 21. The cross-sectional profile of the implant element 41 corresponds to the cross-sectional surface 82 of the implant body, or is slightly smaller in order to ensure easy removal of the implant dummy from the recess.

The implant dummy 36 also has a top surface 43. The distance 46 between the lower surface 41*a* of the implant element 41 and the top surface 43 corresponds to the distance that you get when adding the thickness 14 of the implant body 27 (corresponding to the depth of the recess in the bone plus the thickness of the corresponding cartilage), the height of the guide hole 53 and/or the length 51*a* of the dummy reference 37, taking regard to any overlap between the guide hole 53 and the dummy reference 37 when they are attached. For a demonstration on how the recess depth is checked using the implant dummy 36 together with the dummy reference 37, see below in connection with FIGS. 14*j-p*. In one embodiment the thickness 41*b* of the implant element 41 is the same as the thickness 14 of the implant body 10, such that the recess depth can also be checked directly using the implant element 41 only, i.e. without the dummy reference 37 and top surface 43.

Figures 14E, 14F:
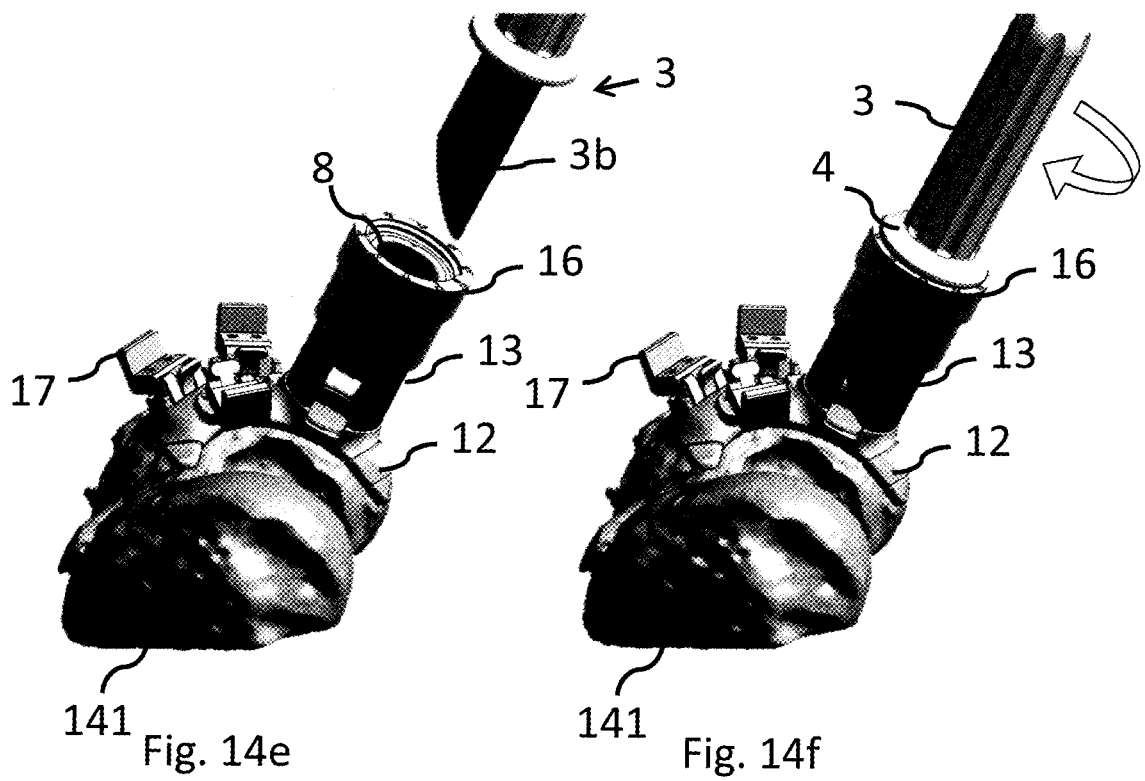
FIG. 14a-t show an exemplifying embodiment of a method for implanting a cartilage implant using the modular surgical kit of the present disclosure.
Figures 14G, 14H:
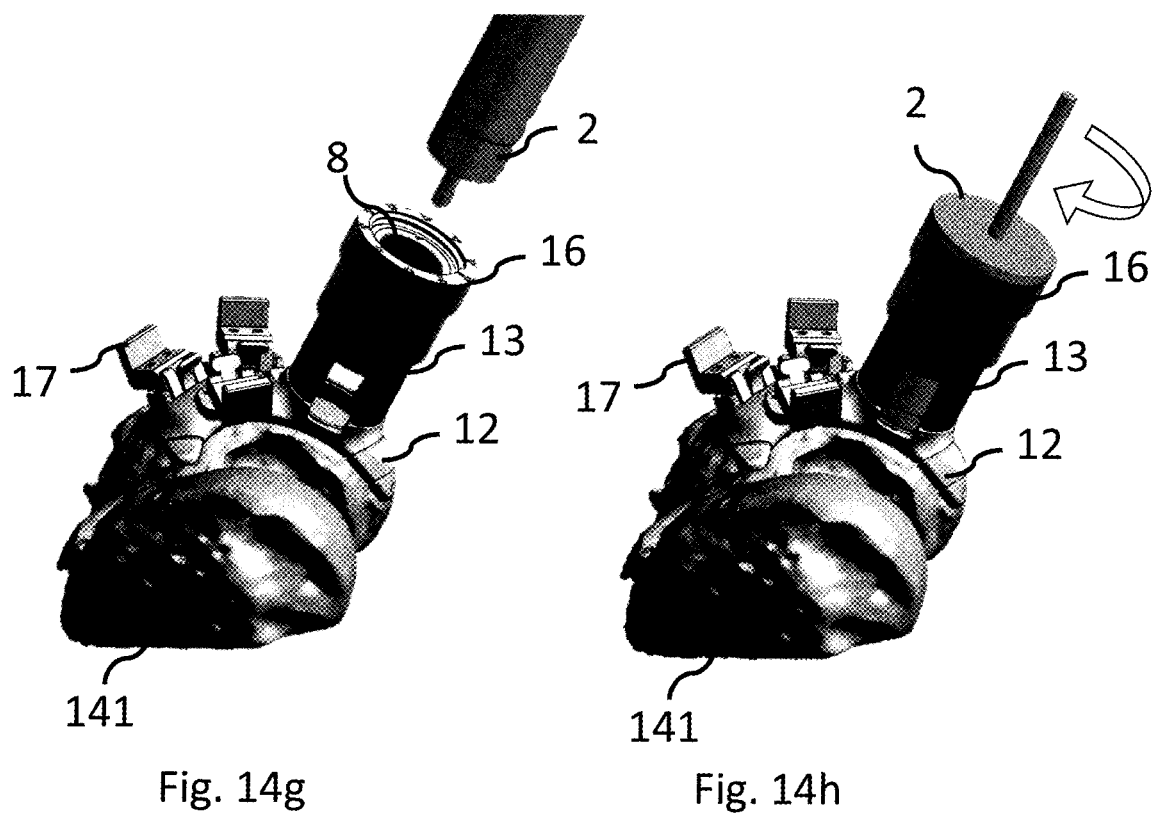
Figure 14I:
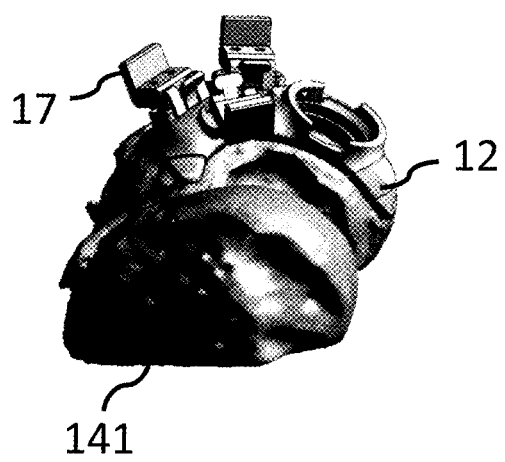
Figure 14J:
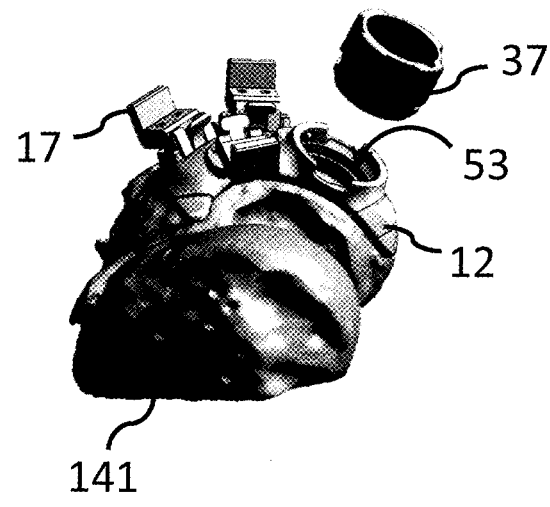
Figure 14K:
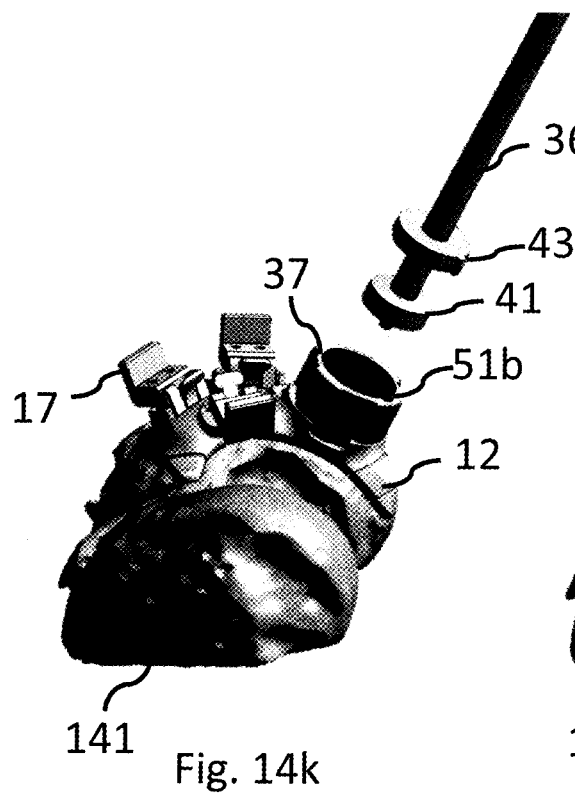

The dummy reference 37, see FIG. 11*a*, is arranged to fit to, and possibly releasably attach to, the guide hole 53 of the guide base 12, see FIGS. 14*j-k*. It is also arranged to receive the implant dummy 36, by being provided with a channel 58. The cross-sectional profile of channel 58 corresponds to the cross-sectional profile of the guide channel 54. Thus the channel 58 is able to receive the implant dummy 36, and also the implant 10, with a slight tolerance that allows a sliding movement of the implant dummy 36 in the channel 58, see FIGS. 13*a-l*, bottom row to the right. The dummy reference 37 and channel 58 has a length 51*a*.

To ensure that the implant dummy 36 is placed in a correct orientation in the recess of the bone, i.e. in an orientation that corresponds to the orientation that the implant 10 is to be inserted in, the top surface 43 and/or the implant element 41 may be provided with some kind of marking or shape fit element 43*a*. A corresponding marking or shape fit element 51*b* is then provided also on the dummy reference and/or the guide base 12.

Mandrel

The mandrel 35 (see FIGS. 2 and 12) consists of a solid body and has a mandrel surface 35*a* that is designed to fit the articulate surface 15 of the implant 10, i.e. it has a corresponding cross-sectional profile and preferably also a corresponding, although inverted, curvature. The mandrel may also be designed to fit the inside of the guide channel 54, with a slight tolerance to allow a sliding movement of the hammer tool 35 in the guide channel 54. The mandrel 35 is preferably used inside the guide channel 54 to hammer the implant in place, for support and to get the proper angle, or may alternatively be used without the support from the guide channel 54, see FIGS. 14*r-s*. The height 68 of the mandrel 35 is in one embodiment the same height 31 as of the guide channel 54. For such embodiment, once the mandrel 35 is hammered in the same level as the top of the guide channel, the hammering and thus the placement of the implant is finished.

The hammer tool 35 may also be accompanied by a hammer tool adapter 34, see FIG. 12, for facilitating the use of the hammer tool and minimizing the absorbtion of the shock caused by the hammer tool and/or minimize the risk of scratching the surface of the implant 10 while hammering. It is made from a soft material that is gentle to the implant surface, e.g. a rubber or plastic material.

Detailed Description of a Method for Implanting the Implant Using the Set of Tools Use of the surgical kit and set of tools disclosed herein will now be further explained in connection with an exemplifying embodiment shown in FIGS. 14*a-t*. The example concerns a surgical kit for implantation of a small implant 10 into a knee joint. The same principles do however apply also for other joints as well as for mosaicplasty surgery. For the latter an implant body 13 with more than one guide channel 54 may be used, and the grafted plug 600 may be a selection of bone and cartilage plugs from a healthy part of the joint, or a selection of artificial implant plugs of various sizes.

Figure 1:
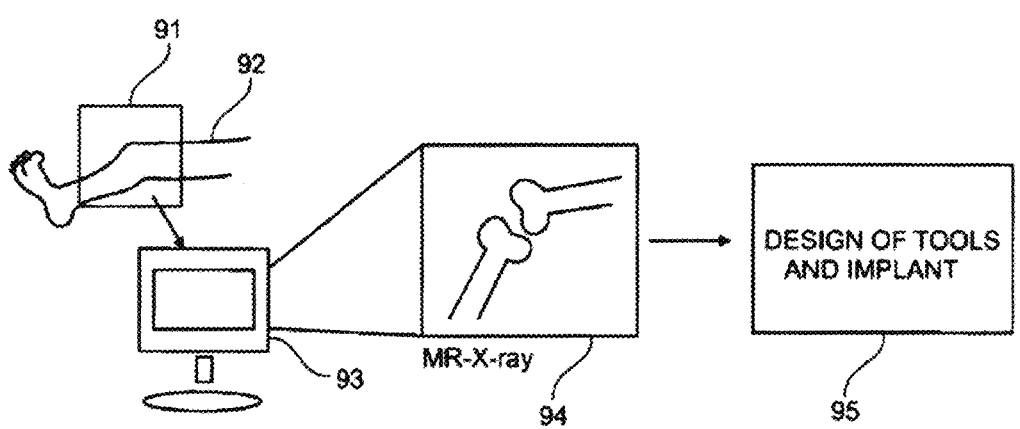
FIG. 1 shows a schematic overview of an exemplifying method used for designing a patient specific surgical kit.

1. Localize the area of the injury and determine the desired size and shape of the implant, see FIG. 1. The position and size of the cartilage damage can be identified by a combination of MRI or CT images or by dGEMRIC technique. The images may then be handled in special surgical planning tool software. All of the parts in the surgical kit may be individual adjusted depending on size of cartilage damage, location of the cartilage damage and also depending on a simulation of the individual surface appearance without damage. Alternatively an implant from a set of predetermined implants may be selected and the set of tools designed or selected thereafter.

2. The implant 10 and set of tools are manufactured depending on; the size of the implant needed, the localization of the injury, the appearance of the cartilage surface intended to be replaced. The designs may be based on the MR images/CT-scanning images from the joint of the person having the cartilage damage, using the surgical planning software. The surgical planning software is connected to manufacturing devices, for example a laser printer, a lathe and/or a reamer, and the parts of the kit are manufactured using e.g. additive manufacturing, laser sintering techniques, turnery or reaming.

3. A surgical opening is made in the leg tissue depending on the localization of the injury and the size of the implant and also depending on the size and conformation of the guide tool.

4. The guide base 12 is placed on the surface of the knee cartilage, see FIG. 14*a*. The guide base 12 fits due to the fact that it is custom made to be placed in that particular position. This allows the surgical procedure (cartilage and bone removal and insertion of the implant) to be performed with good accuracy and precision. If necessary the guide tool can be further stabilized with rivets or pins on a part of the guide tool that is in contact with parts of the joint that have no cartilage tissue. The rivets or pins may also be attached by additional use of adapters 17 that are first attached to the guide base 12 via attachment means 9, see FIG. 14*b*.

5. The guide body 13 is attached to the guide base 12 via the releasable attachment means 47, see FIGS. 14*c-d*. The guide body 13 may further be provided with a drill adjustment device 16 and/or a drill insert 8 that provides a guide channel 54 of the right shape and size, i.e having a cross-sectional profile that corresponds to the cross-sectional profile 81 of the implant that is to be implanted.

6. When the guide body 13 has been attached to the guide base 12, the cartilage cutting tool, here a cartilage cutter 3, is used to cut out a piece of the cartilage that corresponds to the cross-section 81 of the implant 10 that is to be implanted (see FIGS. 14*e-f*). The cartilage cutter body 3*b* fits exactly in the guide channel 54 and thus by turning can make a hole in the cartilage of the desired size and with precision to fit the implant size and at the desired position. A depth gauge 4 on the cartilage cutter 3 can be used in order to help make sure that the cutting is not made too deep.

7. After the piece of cartilage has been removed, the drill and bone remover 2 is then inserted in the guide channel 54, see FIGS. 14*g-h*. When the drill and bone remover 2 is turned/drilled the central drill 22 will give an exact, desired placement of a bore in the bone where the extending post 23 of the implant 10 is to be inserted. The bore is preferably made with a central drill 22 having a slightly smaller diameter than the diameter 18 of the extending post 23 of the implant 10 so that when the implant 10 is hammered in place it will be firmly attached in the bone. When the drill and bone remover 2 is turned/drilled the cutting edge of the bone remover 26 will at the same time create a recess in the bone at the exact desired place and of the desired shape to fit the implant body 27 of the implant 10. Such recess will have a cross-sectional profile that is the same as the cross-sectional profile of the drill and bone remover 2, i.e. the same as the cross-sectional profile of the implant 10.

8. After the drilling and cutting the drill and bone remover 2, as well as the guide body 12 are removed, see FIG. 14*i*. The site of implantation can now readily be cleaned from wear and waste from the drilling and cutting, and inspected to see whether the desired result has been achieved.

9. Now, the implant dummy 36 and dummy reference 37 are used to check whether the recess in the bone is deep enough to receive the implant 10, without the implant 10 projecting over the surface of the surrounding cartilage. The dummy reference 37 is first placed and possibly attached to the guide hole 53 of the guide base 12, see FIGS. 14*j-k*. The implant dummy 36 is then inserted to the channel 58 of the dummy reference 37, such that the implant element 41 is in an orientation corresponding to the orientation in which the implant 10 is to be implanted. This can be ensured e.g. by a marking or shape fit element 43*a* on the implant dummy and a corresponding marking or shape fit element 51*b* on the dummy reference and/or the guide base 12.

Figure 14L:
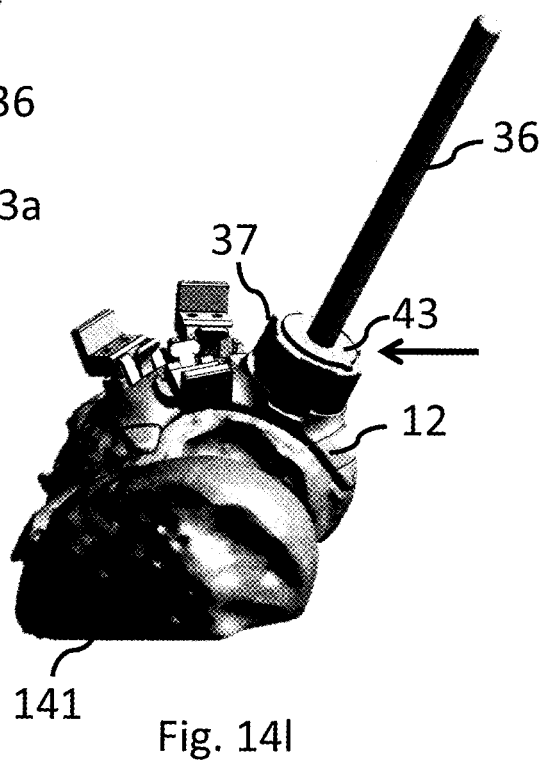
Figures 14M, 14N:
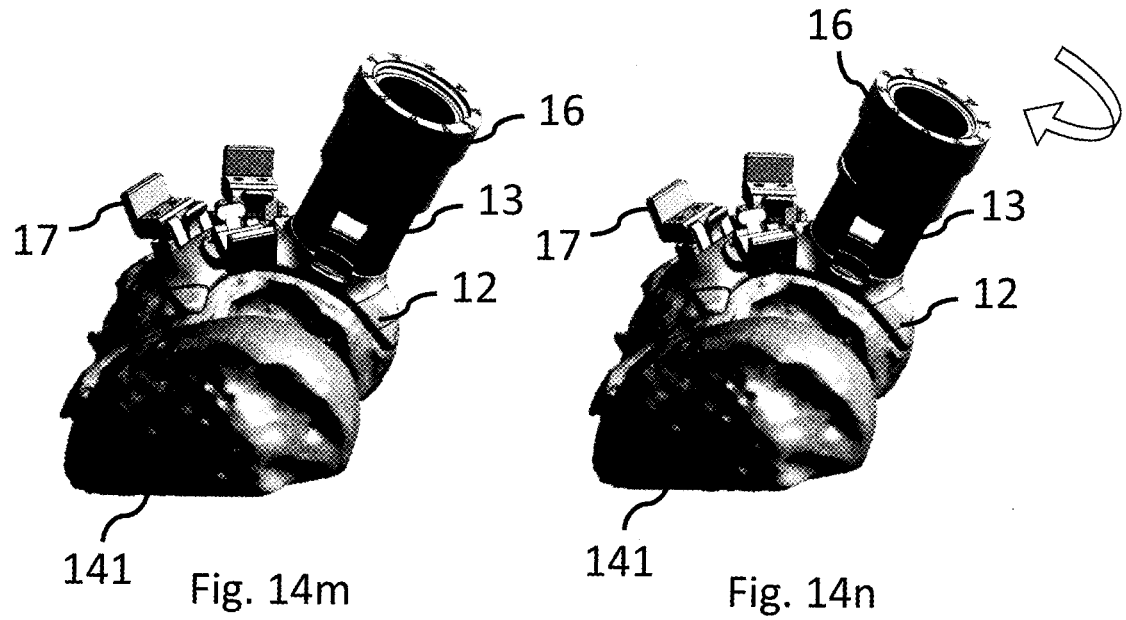
Figures 14O, 14P:
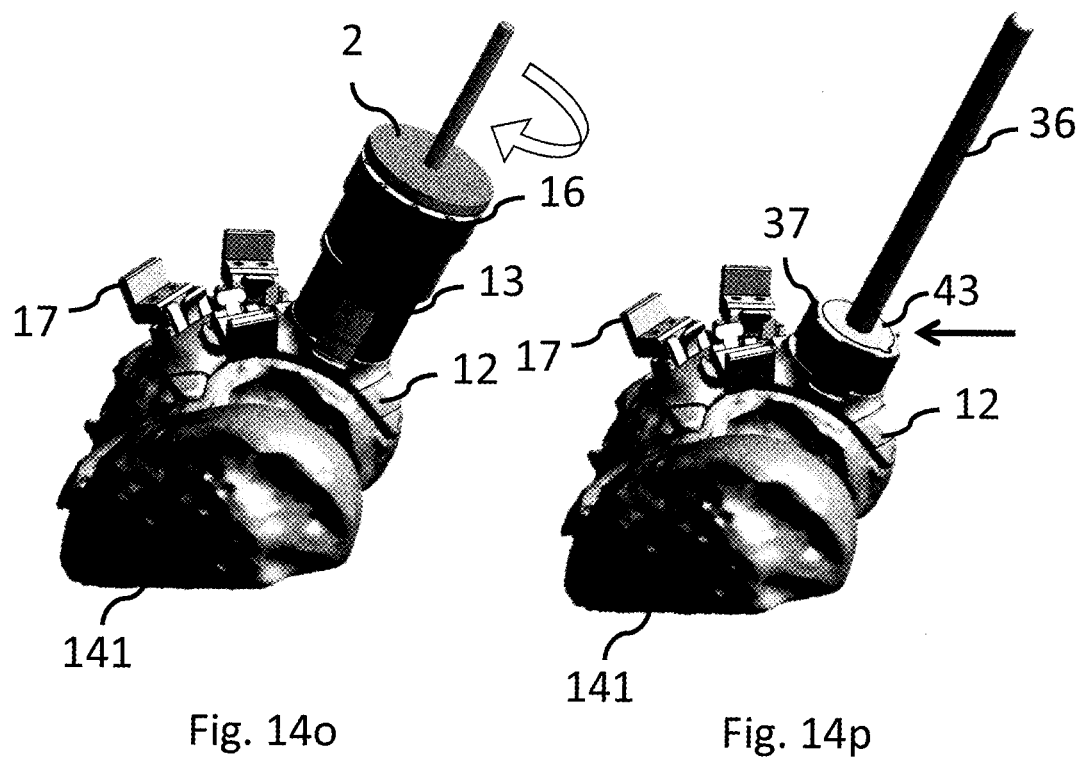

The implant dummy 36 and dummy reference 37 are arranged such that when the depth of the recess in the bone that is to receive the implant body 27 is deep enough the top surface 43 of the implant dummy 36 and the top edge of the dummy reference should lie flush or in line with each other, see arrow in FIGS. 14*l* and 14*p*. This is achieved by arranging the implant dummy 36 and the dummy reference 37 such that the distance 46 between the lower surface 41*a* of the implant element 41 and the top surface 43 corresponds to the distance that you get when adding the thickness 14 of the implant body 27 (corresponding to the depth of the recess in the bone plus the thickness of the corresponding cartilage), the height of the guide hole 53 and/or the length 51*a* of the dummy reference 37, taking regard to any overlap between the guide hole 53 and the dummy reference 37 when they are attached (see also above).

As is seen by the arrow in FIG. 14*l* the top surface 43 of the implant dummy 36 and the top edge of the implant reference do not lie flush, i.e. not in line, with each other. Thus, some more drilling/cutting into the bone should be made. The implant dummy 36 and dummy reference 37 are removed from the guide base 12 and the guide body 13 with drill adjustment device 16 attached again to the guide hole 53, see FIG. 14*m*. The drill adjustment device 16 is then adjusted such that the length 31 of the guide channel 54 is shortened. This may for instance be done by turning the drill adjustment device 16 at a number of preset intervals, e.g. one, two or three times 200 μm, or any other number times any other preset interval, see also above, and FIG. 14*n*.

The drilling and cutting procedure is then repeated; see points 7-8 and FIG. 14*o*, and the implant dummy 36 and dummy reference 37 used to check the drill depth again, see FIG. 14*p*. In FIG. 14*p* the top surface 43 and the top edge of the dummy reference lie flush with each other, see arrow. The recess in the bone then is of suitable depth and is ready to receive the implant 10.

Figures 14Q, 14R:
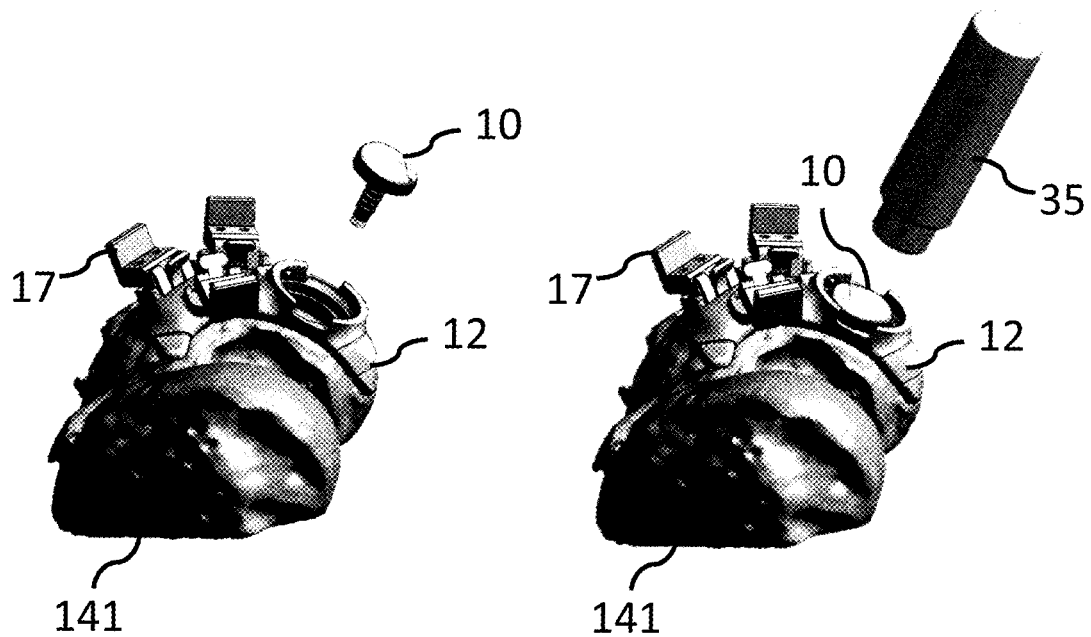
Figures 14S, 14T:
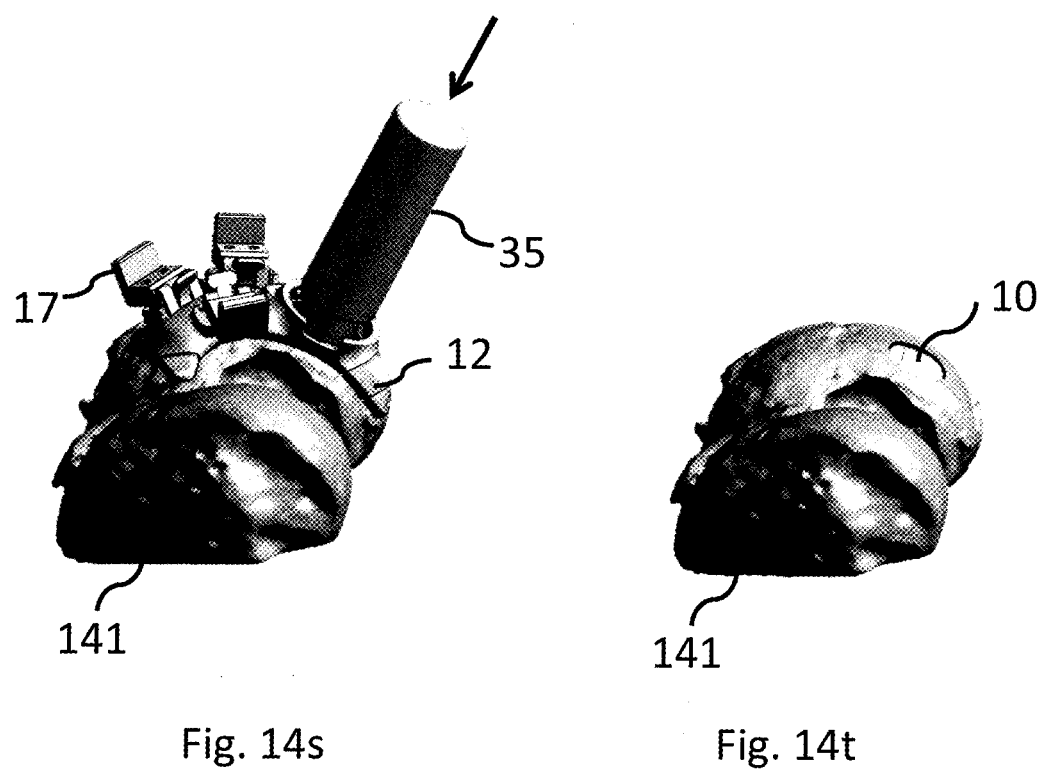

10. The implant 10 may be guided to the exact matching recess at the site of implantation through the guide channel 54 of the guide body 13, or alternatively be placed at the site of implantation without the guide. The later alternative is shown in FIG. 14*q* for illustrative purposes.

11. The mandrel 35 is then used, also either with or without support from the guide channel 54 of the guide body 13, to hammer the implant in position and firmly attach it to the bone. The mandrel 35 is placed on top of the implant 10 and then a hammer or similar tool is used to hammer or push the mandrel 35 (as shown symbolically by the arrow) such that the implant is forced in place, see FIG. 14*s*.

12. Lastly, the hammer tool 35 and the guide base 12 are removed, the implant 10 is implanted at the site of cartilage damage, see FIG. 14*t*, and the incision wound can be stitched.

Further Embodiments

Embodiments comprise a modular surgical kit for repair of diseased cartilage at an articulating surface of a joint, for use with a medical implant (10), a grafted plug (600) or an artificial plug having an implant body (27, 627) with a predetermined cross-sectional profile (81), the modular surgical kit comprising; a guide base (12) having a positioning body (11) with a guide hole (53) through said positioning body (11), wherein:

the positioning body (11) has a cartilage contact surface (50) that is designed to fit the contour of cartilage or subchondral bone in the joint in a predetermined area surrounding the site of diseased cartilage;

the guide hole (53) has a muzzle (29) on the cartilage contact surface (50) at a position corresponding to the site of the diseased cartilage; and a guide body (13) with a guide channel (54), the guide channel (54) having a cross-sectional profile that is designed to correspond to the cross-sectional profile (81) of the implant body (27, 627) and having a muzzle 32;

wherein the positioning body (11) comprises means for releasably connecting (47) to the guide body (13) such that, when connected, the guide channel (54) is positioned in relation to the positioning body (11) such that its muzzle (32) emanates at a site corresponding to the site of implantation into the bone.

Variants of these embodiments comprises one or more of the features:

wherein the cartilage contact surface (50) is custom designed to fit the contour of the cartilage or subchondral bone of a specific patient;

wherein the cartilage contact surface (50) is designed to fit the contour of the cartilage or subchondral bone of an average patient;

wherein the guide body (13) comprises at least two guide channels (54), each guide channel (54) having a cross-sectional profile that is designed to correspond to the respective cross-sectional profile (81) of at least two implant bodies (27, 627);

wherein the guide channel (54) is provided by a guide insert (8) that is designed to fit in the guide body (13);

further comprising a drill adjustment device (16) being arranged to enable adjustment of the drill depth e.g. in certain length intervals;

wherein the positioning body (11) is arranged with at least one breakage means (57) for enabling easy removal of part of the positioning body (11) by tearing, fracturing or similar breakage, such means (57) for example being provided by grooves, slots or perforations or other weakening of the structure;

wherein the positioning body (11) is arranged with at least one attachment means (9) for enabling easy attachment of adaptors, pins and other devices used during surgery, e.g. by snap fit, this embodiment may further comprise adaptors (17) fitting the attachment means (9), for enabling flexible attachment of pins and other devices;

further comprising an insert tool with a cross-sectional profile that is designed to correspond to the cross-sectional profile of the guide channel (54) with a tolerance enabling the insert tool to slide within the guide channel (54);

wherein the insert tool is a cartilage cutting tool 3 with a cross-sectional profile that is designed to correspond to the cross-sectional profile of the guide channel (54) with a tolerance enabling the cartilage cutting tool 3 to slide within the guide channel (54), and comprising a cutting blade with sharp cutting edges 3c able to cut the cartilage in a shape that substantially corresponds to the cross-section (81) of the implant body (27);

wherein the insert tool is a drill and bone remover (2) with a drill and bone remover body 20 having a cross-sectional profile that is designed to correspond to the cross-sectional profile of the guide channel (54) with a tolerance enabling the drill and bone remover (2) to slide within the guide channel (54), the drill and bone remover (2) further comprising a central drill (22), for drilling a bore to receive the extending post (23) of the implant (10), and a bone remover (26) for cutting a recess in the bone to receive the implant body (27) of the implant (10);

wherein the insert tool is a mandrel (35) with a mandrel surface (35a) that is designed to fit the articulate surface (15) of the implant (10) and having a cross-sectional profile that is designed to correspond to the cross-sectional profile of the guide channel (54) with a tolerance enabling the mandrel (35) to slide within the guide channel (54);

further comprising an implant dummy 36 with an implant element 41 that is designed to match the implant body 27 and having a lower surface 41a that is a replica of the bone contact surface 21, but comprising no extending post 23;

further comprising a dummy reference 37 that is arranged to fit to, and possibly releasably attach to, the guide hole 53 of the guide base 12 and is arranged to receive the implant dummy 36, by being provided with a channel 58.

Further Embodiments of Drill Bit

Embodiments describe an implant specific drill bit 202, see FIGS. 15-18b, which is a combination of a drill and bone remover that is used to drill a recess, a hole or bone cavity in the bone at the site of cartilage damage, for example in a joint in a patient. The recess made is in the same size and shape as the implant, or slightly smaller than the implant, and is intended to be used for fastening and/or implanting an implant with a press fit. A suitable implant 210 to be implanted according to the disclosure, see FIGS. 16b, 18b, comprises an extending post 223 and an implant body 227 and is to inserted in the recess formed using the implant specific drill bit 202 according to the disclosure, in the bone tissue 232 and cartilage tissue 234 in the joint, see FIG. 17.

Figure 15:
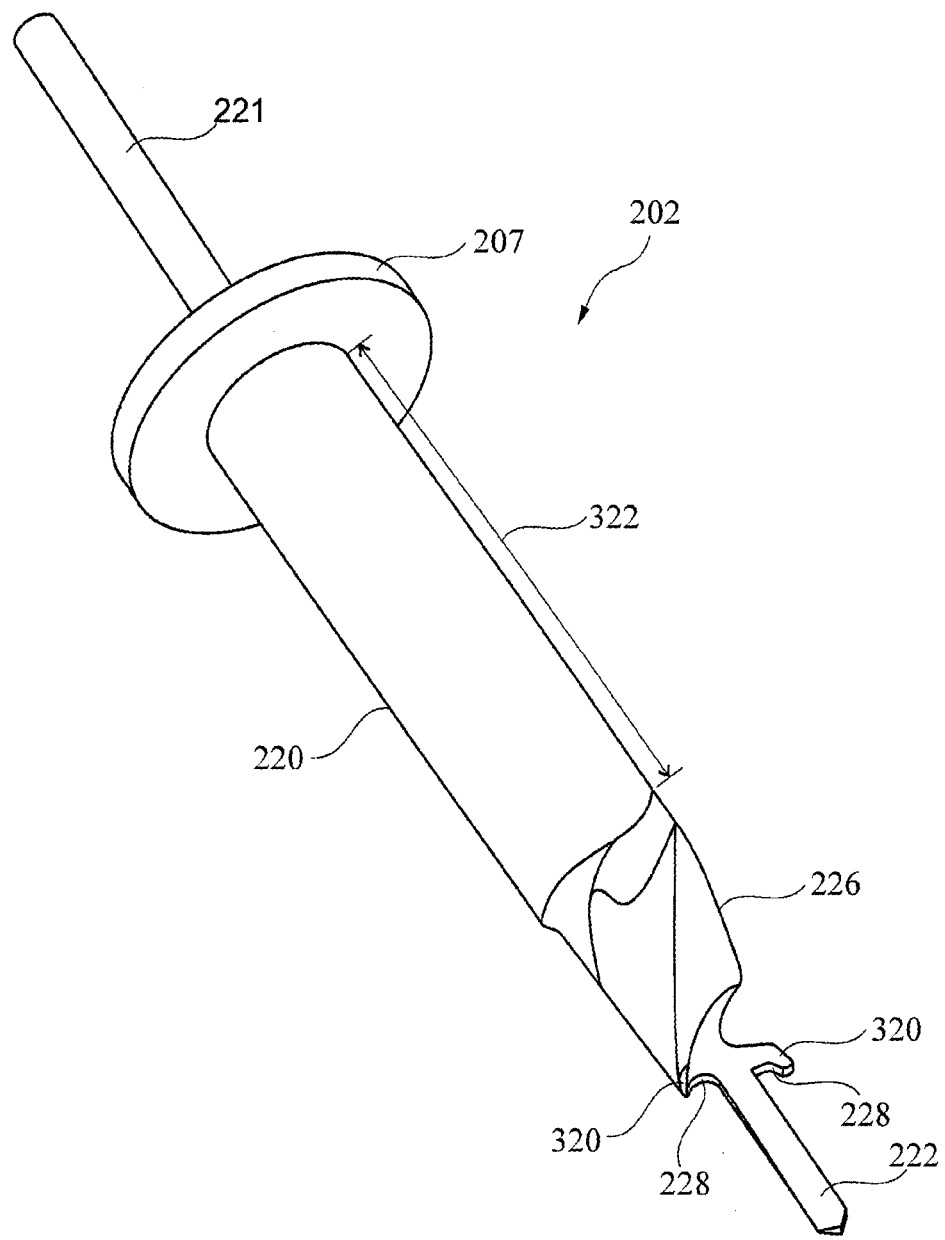
FIG. 15 schematically illustrates an implant specific drill bit according to an exemplified embodiment.

The implant specific drill bit 202 according to the disclosure comprises a drill and bone remover body 220, a central drill part 222 and a bone remover part 226, as shown in FIG. 15. The central drill part 222 extends from the center of the drill and the bone remover body 220 has a proximal end and a distal end and a longitudinal y-axis extending between the proximal end and the distal end, i.e. corresponding to the position of a centrally placed extending post 223 on an implant 210 having a circular implant body 227 when the drill bit is used for drilling a recess.

The implant specific drill bit 202 may for example have the following measures: a drill and bone remover body 220 may be 3-40 mm or 5-40 mm in diameter approximately corresponding to the diameter of the specific implant body 227, or for example 1-5% smaller diameter than the specific implant. The drill and bone remover body 220 may have a length 322 of 2-500 mm or 4 mm-3 cm or 4 mm-5 cm or a length which the drill bit sufficient support when used together with a guide tool in a guide channel. The bone remover part 226 may have similar diameter than the bone remover body 220 or slightly less.

Figure 17:
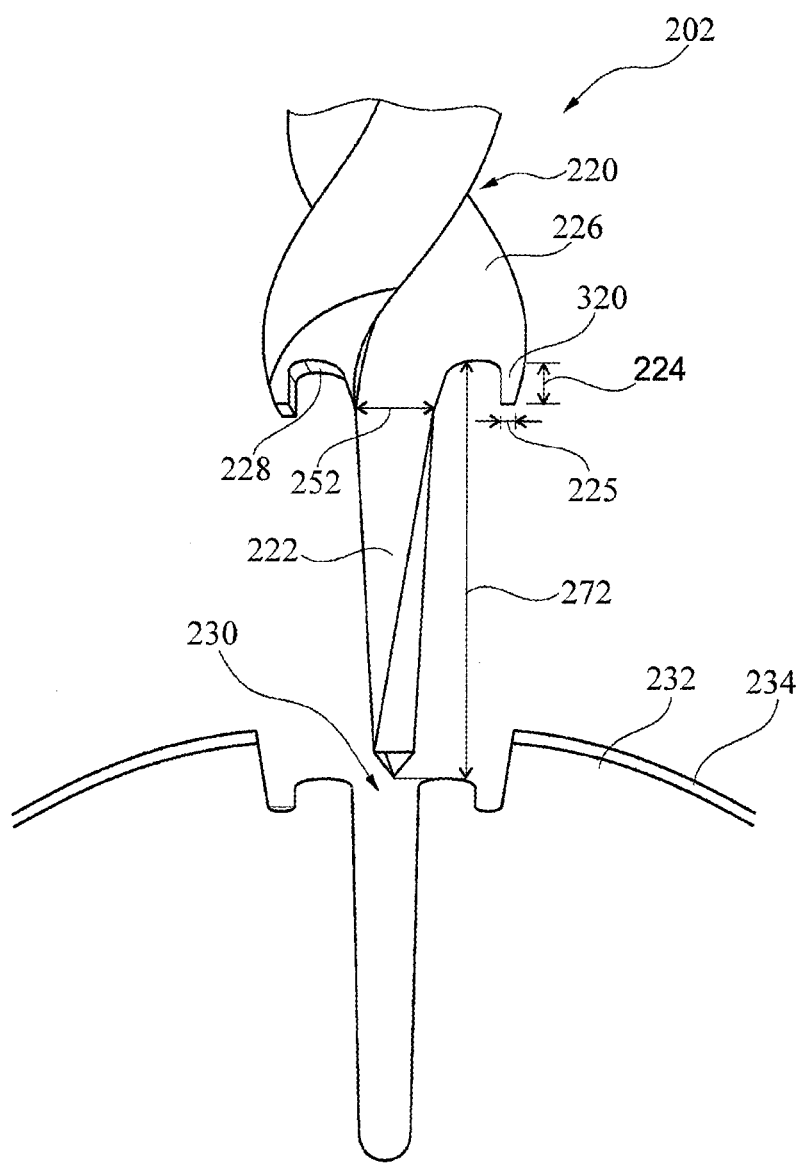
FIG. 17 schematically illustrates use of an implant specific drill bit for creation of a recess in a joint.

The central drill part 222 may be cylindrical or conical in shape and be 0.7-10 mm in diameter (if conical shape, the diameter refers to the broadest part) and have a length 272 of 2-300 mm mm or may have a diameter 252 20% less than the diameter of the drill and bone remover body 220 or the bone remover part, see for example FIG. 17.

The bone remover part 226 comprises a shape cutting edge 228 and the shape cutting edge may further comprise protruding flanges 320 which protrudes from cutting edge surface with a length 324 approximately 0.3-3 mm and a width 326 of 0.3-1.5 mm or 0.3-2 mm, see for example FIG. 17. The protruding flanges 320 is made of a material suitable for cutting bone, for example stainless steel and may have the same material as the shape cutting edge 228.

In one alternative embodiment, as illustrated in FIG. 19b the angle 328 between the shape cutting edge 228 and the longitudinal y-axis 270 of the implant specific drill bit 202 is 90° or less.

If the implant to be implanted has a curved articulating surface 229 the angle 328 between the shape cutting edge 228 and the longitudinal y-axis 270 of the implant specific drill bit 202 is preferably 80° or less in order to keep the volume of the implant body lower.

The implant specific drill bit further comprises a shaft 221 which may have suitable measures and shapes to fit for using together with a drilling machine.

The drill bit according to the disclosure is implant specific. The diameter of the central drill part 222 is the same as, or slightly smaller than, the diameter of the extending post 223 of the implant 210 that is selected to be implanted in the joint. The bone remover 226 of the bone remover body 220 has a shape cutting edge 228 that is placed peripherally around the central drill part 222. The diameter of the bone remover 226 is the same as, or slightly smaller than, the diameter of the implant body 227 of the implant 210 that is to be implanted, thus creating a recess that matches the implant body, in which the implant body can be received. See FIGS. 16a and 16b and FIGS. 18a and 18b for schematic illustrations of an implant and an implant specific drill bit 202 according to the disclosure. The shape cutting edge or blade 228 of the bone remover 226 and the central drill part 222 is hard enough for cutting or carving bone.

The implant specific drill bit 202 according to the disclosure may be made of materials such as stainless steel. The shape cutting edge or blade 228 of the implant specific drill bit or implant specific drill bit 202 according to the disclosure is designed in the same shape as an implant body which is selected to be implanted in the bone cavity made using the implant specific drill bit.

Figures 16A, 16B:
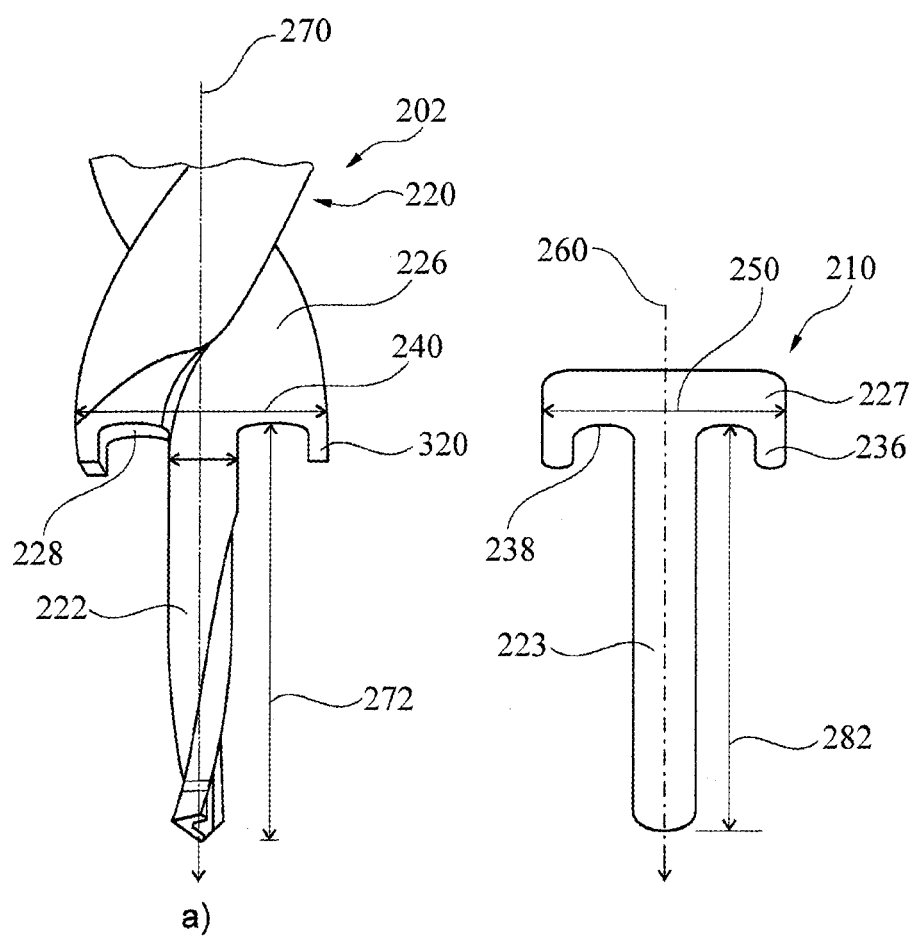
FIG. 16a schematically illustrates an implant specific drill bit according to an exemplified embodiment.
FIG. 16b schematically illustrates an implant for implantation according to an exemplified embodiment.

The shape cutting edge or blade 228 of the implant specific drill bit 202 may be flat (see FIG. 18a) if the implant to be inserted comprises a flat bone contacting surface 238 or shape cutting edge or blade 228 may protrude from the bone remover forming flanges 320, see FIG. 16a if the implant body 227 of the implant to be inserted comprises a shape cutting edge or blade 228 formed as a protruding anchoring ring portion 236 or rim 236, see FIG. 16b. The implant specific drill bit 202 according to the disclosure is designed after the shape of the implant to be inserted.

The drill and bone remover body 220 is constructed for forming a bone cavity for an implant directly in a joint and may alternatively be designed to fit the inside of a guide instrument for example inside a guide channel of a guide body of a guide instrument, with a slight tolerance to allow a sliding movement of the implant specific drill bit 202 in such a guide channel. The implant specific drill bit 202 may also be equipped with a depth gauge 207 and may be used together with a guide tool. The depth gauge 207 of the implant specific drill bit determines the depth of the created drill hole as well as the depth of the recess for the implant body 227.

The cross-sectional profile of the drill and bone remover body 220, the bone remover part 226, the shape cutting edge 228 and the central drill part 222 matches or is slightly smaller, for example 0.1-5 volume % smaller than the cross-sectional profile of an implant 210 and its extending post 223, its implant body 227 and also matches the shape of the implant body which further may comprise an anchoring ring portion 236. The fit ensures the correct, desired placement of the implant specific drill bit 202 on the cartilage surface and thus ensures the precise direction and placement of the drill hole for the extending post 223, as well as the recess for the implant body 227, in the bone.

The depth of the drilling may be adjusted manually if an implant specific drill bit 202 is used that does not comprise a depth gauge 207 and if the drill bit is used without guidance of a guide tool.

A Design Method Designing the Implant Specific Drill Bit 202

A design method according to embodiments comprises the following steps;

determining or selecting a size and shape of an orthopedic implant 210 comprising a circular shaped implant body 227 and a centrally placed circular shaped extending post 223 protruding from the bone contacting surface 238 in a longitudinal y-axis 260 direction of the implant 210; and a. designing the size and shape of said implant specific drill bit 202 comprising a bone remover part 226, a central drill part 222 and a shape cutting edge 228 located one surface of the bone remover part 226, and wherein the central drill part 222 protrudes from the shape cutting edge 228 surface in a longitudinal y-axis 270 direction of the implant specific drill bit 202 depending on the selected size and shape for said implant 210 in determined or selected step a, wherein;

the width 240 of the broadest part of the bone remover 226 in a side view corresponds to, or is slightly smaller than, the diameter 250 of the implant body 227 of the implant 210 that is to be implanted;

the rotational volume and the length 272 of the central drill part 222 corresponds to, or is slightly smaller than, the diameter 252 of the extending post 223 of the implant 210 that is to be implanted;

the curvature of the shape cutting edge 228 that is placed anywhere peripherally around or surrounding the central drill part 222 of the implant specific drill bit 202 corresponds to the curvature of the bone contacting surface 238 of the implant.

Figures 20A, 20B:
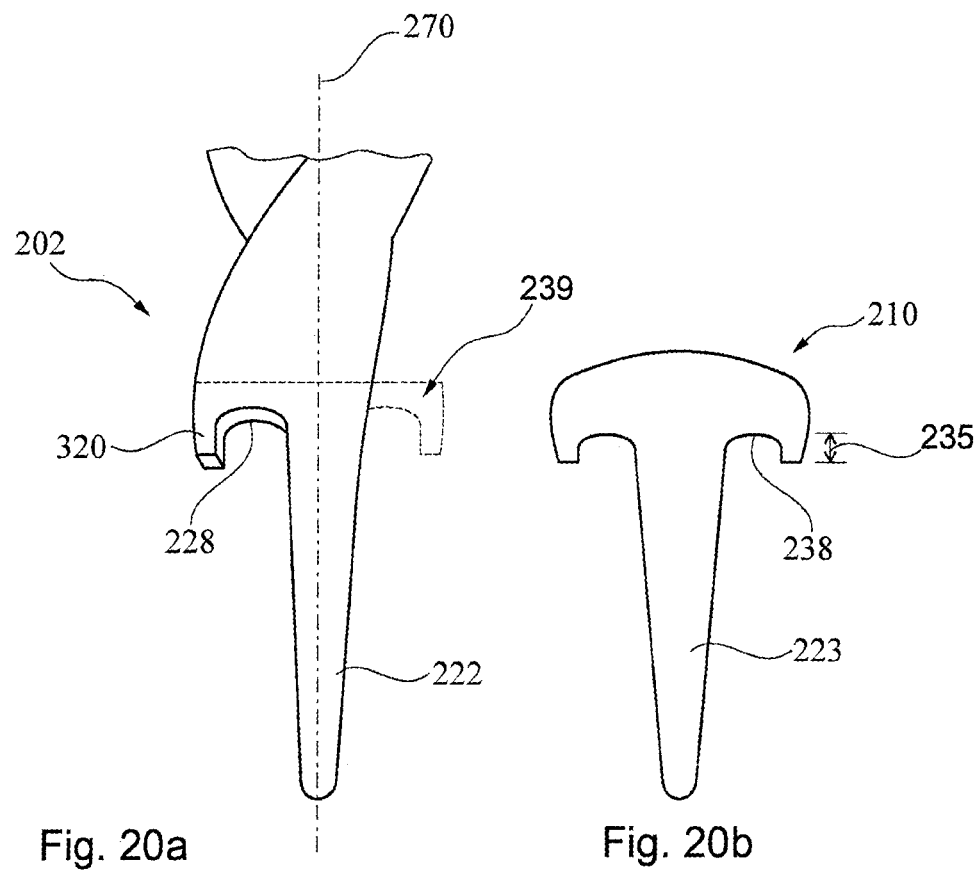
FIG. 20a shows an exemplified embodiment of an implant specific drill bit comprising a cutting edge on only one side of the longitudinal y-axis of the drill bit and having the rotational volume corresponding to the specific implant.
FIG. 20b schematically illustrates an implant for implantation according to an exemplified embodiment.
Figure 20C:
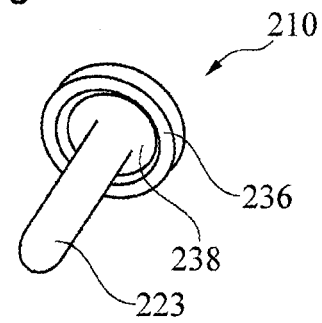
FIG. 20c shows a perspective view of the implant in FIG. 20b.

The rotational volume 239 is a fictive volume, which is illustrated in FIG. 20a, and which is achieved by rotating the implant specific drill bit 202 around its longitudinal axis 270. In embodiments the construction of the drill bit is not symmetrical in shape as the construction of the specific implant. The rotational volume of the implant specific drill bit is symmetrical and is designed to correspond to the volume of the specific implant. This rotational volume (239) also corresponds to the volume that is removed when the implant specific drill bit 202 according to the disclosure is used for drilling a cavity 230 in the bone and or the cartilage in the joint. The rotational volume is therefore a copy of the volume and size and shape of the implant (comprising an implant body and the extending post etc., even though the implant specific drill bit 202, when not rotated, may have another shape than the implant. See also FIG. 17.

The implant may be selected from a kit of implants of different shapes and sizes or may be designed to fit a specific cartilage damage in a specific patient. Individually constructed implants are made by investigation of the joint using for example MR and then using that data to create an implant body which will be sufficient to repair the cartilage damage in that specific patient.

FIG. 20a shows an exemplified embodiment of an implant specific drill bit comprising a shape cutting edge on only one side of the longitudinal y-axis of the drill bit and having the rotational volume corresponding to the specific implant.

A design method according to the disclosure for designing the implant specific drill bit 202 may comprise a step wherein the shape cutting edge 228 of the drill bit 202 is designed to correspond to the shape and curvature of an implant with a bone contacting surface 238 which is flat or a an implant 210 with a bone contacting surface 238 which comprises an protruding anchoring ring portion 236.

An implant with a protruding anchoring ring portion 236 is very well anchored in the bone cavity since both the extending post and the protruding anchoring ring portion 236 of the implant is contributing in fastening of the implant placed in a joint.

The shape and size of the implant are calculated or selected dependent on the size and shape of the cartilage damage, and dependent on the curvature of the contour of the cartilage and/or of the subchondral bone in the area substantially coinciding with the cartilage damage.

The following steps may be comprised in generating design parameters for an implant specific drill bit according to the disclosure:

Generating a cross-section for the bone remover part 226 of the implant specific drill bit 202 dependent on and substantially corresponding to said determined cross-section of the implant body 227 of an implant 210. The cross-section for the implant body is generated or selected from a kit of implants to correspond to the cross-section shape determined for the cartilage damage.

Generating a length and a cross-section profile for a specific drill bit 222 wherein the specific drill bit 222 is extending from a shape cutting blade or edge 228 of the implant specific drill bit 202 and is dependent on or corresponding to, the length and cross-section profile for an extending post 223 of an implant. The size and shape of the extending post is selected automatically according to a predetermined scheme or is selected manually by an operator.

Generating the shape of a shape cutting blade or edge 228 of an implant specific drill bit 202 may be flat or comprise protruding flanges 320 depending on, or corresponding to the size and shape and curvature of the bone contacting surface 238 of an implant 210.

Figures 18A, 18B:
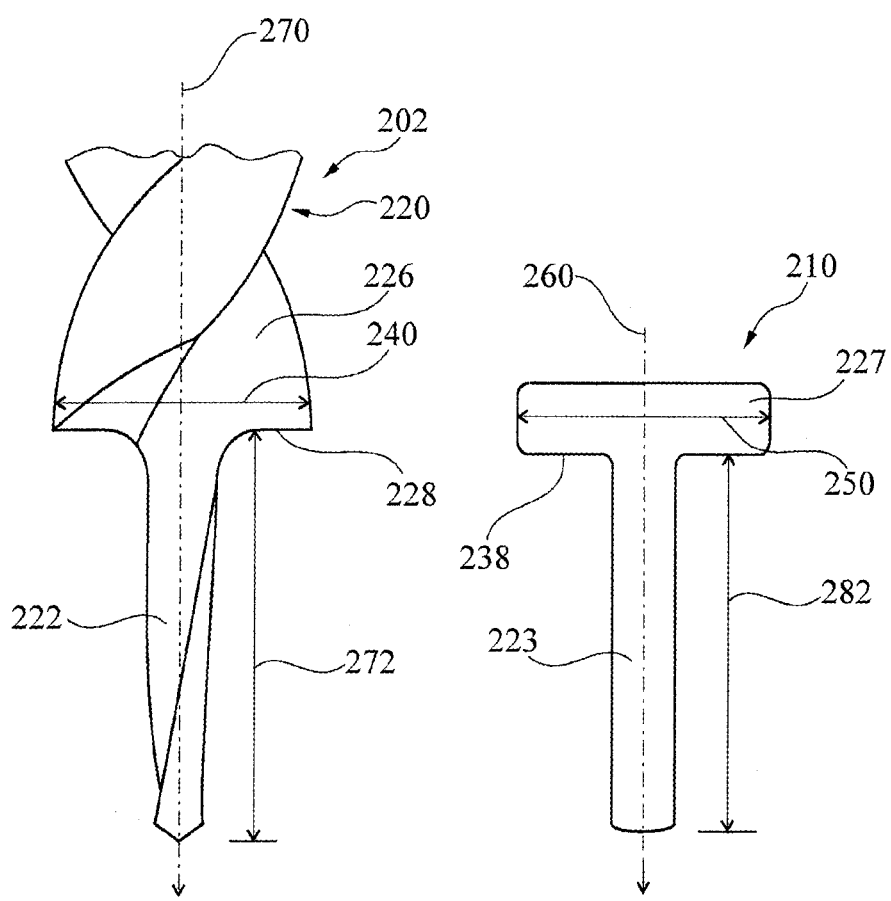
FIG. 18a schematically illustrates an implant specific drill bit according to an exemplified embodiment.
FIG. 18b schematically illustrates an implant for implantation according to an exemplified embodiment.

FIGS. 16a and 16b and also FIGS. 18a and 18b show examples of the size and shape of an implant specific drill bit 202 which is designed dependent of or corresponding to the design; the shape, size and curvature of an implant 210.

The length of the implant specific drill bit 202 is depending on the need for a long or short shaft for attaching the drill bit to a drill.

The length of the drill and bone remover body 220 is selected dependent on the intended use of the implant specific drill bit 202. The length is preferably longer than the depth or height of the implant body of the implant intended to be implanted. For example a use of the implant specific drill bit 202 inside a guide tool guiding and supporting the drill bit may lead to a design of a drill and bone remover body 220 which corresponds to the length of a guide channel of such a guide tool, for maximum support of the drill bit during drilling.

Determination of the cartilage damage and alternative embodiments generating design parameters of a medical implant 210 and thereby generating design parameters for an implant specific drill bit.

An image or a plurality of images representing a three dimensional image of a bone member of the joint in a patient's limb is obtained by selecting one of a per se known imaging technology for non-invasive imaging of joints, such as magnetic resonance imaging (MRI), computerized tomography (CT) imaging or a combination of both, or other suitable techniques such as delayed Gadolinium-enhanced MRI of cartilage (dGEMRIC) techniques. The image of the joint should comprise a representation of cartilage in the joint as well as the underlying subchondral bone in the area of the cartilage damage. Image data making up a three dimensional image representation of the joint is stored in a digital format in a manner that enables to keep track of the dimensions of the real joint that the image depicts.

The image data is analyzed in a data processing system to identify and determine physical parameters for the cartilage damage. The physical parameters to determine comprise the presence, the location and the size and shape of the cartilage damage, as well as curvature of the surface contour of the cartilage or the subchondral bone in an area of the cartilage damage.

In one embodiment of the inventive concept the design system operates to determine physical parameters on images of the patient's individual joint and the current cartilage damage, and thereby produces an individually designed implants which shape and size is used as model for designing shape and size of the implant specific drill bit 202 according to the disclosure.

Further in one exemplified embodiment, the contour curvature for an articulate surface of a substantially plate shaped implant body 227 dependent on said determined surface curvature of the cartilage and/or the subchondral bone.

The contour curvature for the articulate surface of the implant body is generated to correspond to the curvature that covers the cartilage damage.

In another embodiment the design system operates on a collection of images of joints constituting a statistical basis for determining physical parameters for producing an implant 210 which then is used as a model for designing an implant specific drill bit according to the disclosure.

Embodiments comprises a design method designing an implant specific drill bit 202 comprising:
  determining or selecting a size and shape of an orthopedic implant 210 comprising a circular shaped implant body 227 and a centrally placed circular shaped extending post 223 protruding from the bone contacting surface 238 in a longitudinal y-axis 260 direction of the implant 210; and
  selecting design parameters for the implant specific drill bit 202 by:
  selecting the width 240 of the broadest part of the bone remover 226 in a side view to correspond to, or to be slightly smaller than, the diameter 250 of the implant body 227 of the specific implant 210 that is to be implanted
  selecting the rotational volume and the length 272 of the central drill part 222 to correspond to, or to be slightly smaller than, the diameter 252 of the extending post 223 of the specific implant 210 that is to be implanted
  selecting the curvature of the shape cutting edge 228 that is placed anywhere peripherally around or surrounding the central drill part 222 of the implant specific drill bit 202 to correspond to the curvature of the bone contacting surface 238 of the implant.

In further embodiments the determining the size and shape of said implant may either be performed by:
  selecting implants from a kit of implants of different predetermined sizes; or
  by individually designing the size and shape of an implant;
and wherein the size and shape of the selected implant is corresponding in large or partly or substantially to the size and shape of a cartilage damage in a specific patient.

Further embodiments may comprise:
  wherein said shape cutting edge 228 in side view is designed to correspond to the shape of at least one side of the bone contacting surface 238 in a cross-sectional view of the specific implant 210; and wherein the bone contacting surface 238 is substantially flat or a bone contacting surface 238 which comprises an protruding anchoring ring portion 236.
  wherein the volume of the part of the designed implant specific drill bit 202 which corresponds to fit the implant 210 is 0.1-5% smaller than the volume of the implant 210 to be implanted, allowing for press fit of the implant 210 placed in the recess made by the implant specific drill bit 202 according to the disclosure.
  wherein the shape cutting edge comprises at least one flange 320.
  wherein the flange has a length 224 of 0.3-3 mm protruding from the shape cutting edge 228 and/or a width 225 of 0.3-2.0 mm or 0.3-2.0 mm corresponding to the length 235 in a cross-sectional view of the anchoring ring portion 236 of an implant 210.
  wherein the angle 328 between the shape cutting edge 228 and the longitudinal y-axis 270 of the implant specific drill bit 202 is designed to be 90° or less or for example 80° or less or 70° or less based on the selected specific implant and its corresponding angle.
  wherein the length 272 of the central drill part 222 of the implant specific drill bit is designed to be 2-300 mm corresponding to or slightly longer, or 1-5% longer than the length 282 of the extending post 223 of an specific implant 210.

Further embodiments comprises an implant specific drill bit 202 designed according to the design method in any of the above embodiments for producing bone cavities for receiving orthopedic implants, said drill bit 202 comprises:
  a drill and bone remover body 220 having a proximal end and a distal end and a longitudinal axis extending between the proximal end and the distal end; and
  a bone remover part 226 located in one end of the bone remover body 220; and a central drill part 222 protruding from said bone remover part 226;
wherein said bone remover part 226 comprises a shape cutting edge 228 which is placed peripherally around the central drill part 222. The bone remover part 226 may comprise a flat surface or a surface which further comprises flanges 320.

One embodiment comprises a kit comprising an implant specific drill bit 202 designed according to any of the above method embodiments and an implant 210, wherein said an implant specific drill bit (202) is designed to correspond to the size and shape of said implant 210.

Figure 21:
FIG. 21 shows an example of a recess in cartilage and bone tissue drilled with conventional drilling tools having frayed cartilage and misaligned cartilage and bone tissue recesses.
Figure 22:
FIG. 22 shows an example of two adjacent recesses drilled with drill tools of embodiments drill tools presented herein.

FIG. 21 shows an image of a recess drilled in a cartilage coated bone tissue with a conventional drill, the edges of the recess is uneven and the cartilage is frayed. Further, with conventional technology the edges of recess in the cartilage may be misaligned relative the edges of the recess of the bone tissue. The embodiments described herein improve the alignment of the recesses in the cartilage and the bone tissue, as shown in FIG. 22.

Figure 24B:
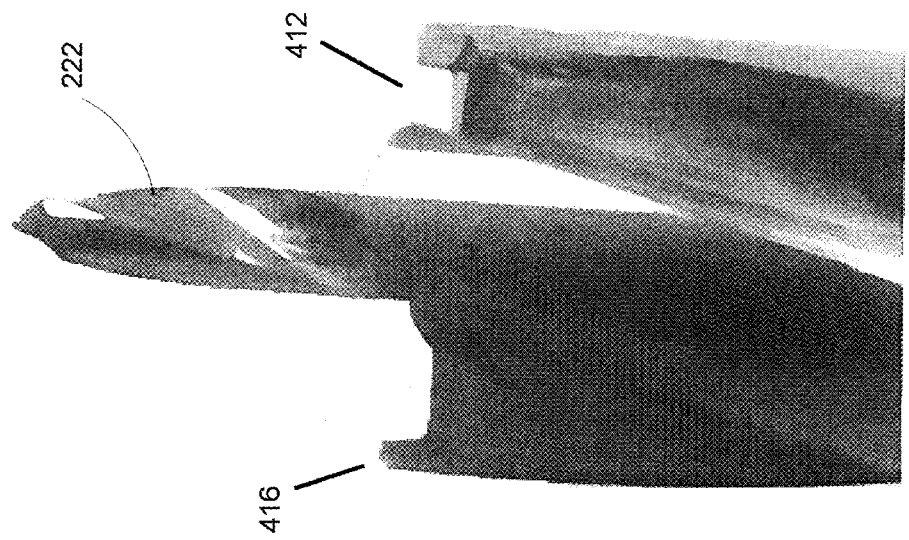
FIGS. 24a and 24b show images of an embodiment of a drill tool with sharp pre-cutting edges and shark fin shape forming edges.
Figure 24A:
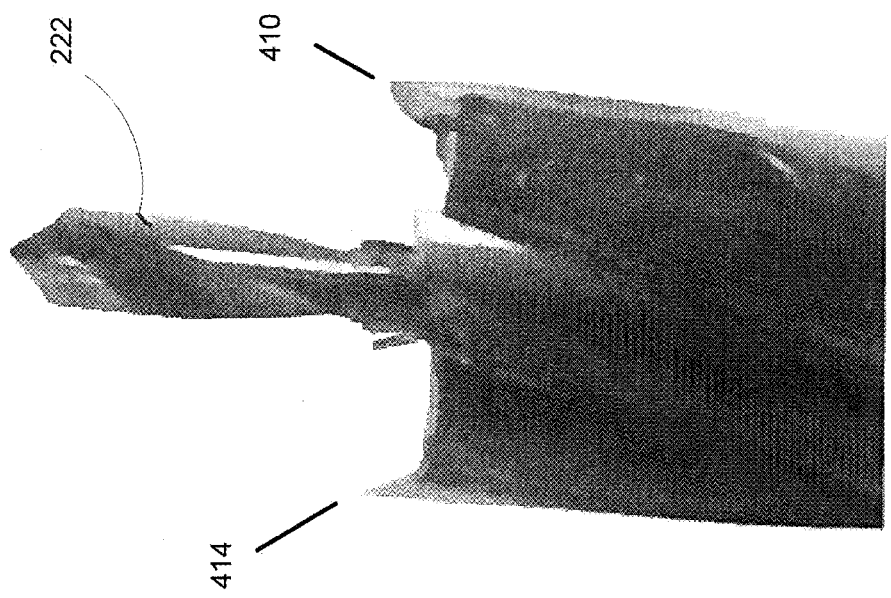

FIG. 23 shows an embodiment of the lower part of a drill bit 202 having sharp pre-cutting edges 410, 414 and shark fin shape cutting edges 412, 416. The pre-cutting edges 410, 414 protrude, for example in the range of 0.1 to 1 mm such as 0.5 mm, in relation to the shark fin shape cutting edges 412, 416 in order to cut through the cartilage before cutting the recess in the bone tissue. Different embodiments comprise one or more cutting edges, for example three or four cutting edges. In embodiments each shape cutting edge 228 is paired with an associated sharp precutting edge 410, 414. FIG. 24a and FIG. 24b show images of an embodiment of such a drill bit. In FIG. 24a the sharp cutting edges 410 and 414 are indicated, whereas FIG. 24b shows the drill bit turned 45 degrees around its rotational axis and the shark fin shape cutting edges 412 and 416 being visible. In embodiments, the sharp pre-cutting edges 410, 414 of the drill are longer, for example 0.2 mm longer, than the shark fins (edges) of the implant's hat in order to provide a gap under the implant. In embodiments, the thickness of the shark fin shape cutting edges 412, 416 are wider, for example 0.2 mm wider, than the shark fins (edges) of the implant's hat in order to allow fitting the implant in the recess.

FIG. 25a and FIG. 25b shows how the shape of the lower part of the drill 202 corresponds to the bone contacting part of the implant 210.

Embodiments of the kit comprises a drill guide having guides for one, two or more adjacently positioned bores. The kit and/or its parts enable the creation of a recess with desired angle or tilting in relation to the surface of the cartilage and/or bone. The kit and/or its parts enable removal of tissue to match the geometry of an implant. Embodiments of the drill enables the drilling of a two parallel bores to make a recess for an implant with a hat and an extending post. Embodiments of the drill comprises a drill body with 220 with a diameter smaller, for example 0.2 mm smaller, than the diameter of the hat of an associated implant in order to provide a press fit of the implant in the recess in the bone tissue. Embodiments of the drill comprises a drill peg 222 having a smaller diameter, for example 0.4 mm smaller, and having a longer extension, for example 2 mm longer, than the peg or post of an associated implant in order to provide a press fit for the implant with the bone tissue. Embodiments of the drill comprises a sharp tip in order to avoid slipping on the cartilage surface. Embodiments of the drill comprises one or more flutes enabling removal of tissue during drilling. In embodiments of the drill, all or some of the edges of the drill stop and/or shaft shall be broken/chamfered/rounded. In embodiments, the large drill diameter and/or the drill peg has a part of its peripheral surface area offset inwards in order to minimize friction during drilling.

The invention claimed is:

1. A drill tool for implant surgery comprising a drill bit having a longitudinal y-axis, a proximal end, and a distal end opposite the proximal end in the longitudinal y-axis, the drill bit comprising:
   a first drill part adjacent the distal end and comprising one or more cutting edges configured to drill a first diameter recess; and
   a second drill part further from the distal end than the first drill part and comprising:
      one or more shape cutting edges facing the distal end along the longitudinal y-axis and configured to drill a second diameter recess; and
      one or more sharp pre-cutting edges extending 0.3 to 3 mm from each of the one or more shape cutting edges towards the distal end in the longitudinal y-axis and configured to extend a portion of the second diameter recess along the longitudinal y-axis without increasing the size of the first diameter recess,
   wherein a shortest diameter of the second diameter recess is larger than a largest diameter of the first diameter recess.

2. The drill tool according to claim 1, wherein an angle between the one or more shape cutting edges and the longitudinal y-axis of the drill tool is designed to be 90° or less.

3. The drill tool according to claim 1, wherein the first diameter recess is adapted for an implant body of a specific implant to be implanted and the second diameter recess is adapted for an implant post of a specific implant to be implanted.

4. The drill tool according to claim 3, wherein the second diameter recess has a depth defined by the thickness of the implant body between an articulating surface of the implant body and a bone contact surface of the implant body, the bone contacting side being opposite to the articulating surface.

5. The drill tool according to claim 3, wherein:
   the second diameter recess that the one or more shape cutting edges and the one or more sharp pre-cutting edges are arranged to drill corresponds to, or is slightly smaller than, a diameter of the implant body to provide firm attachment in the bone;
   the first diameter recess that the one or more cutting edges of the first drill part are arranged to drill corresponds to, or is slightly smaller than, a diameter of the implant post to provide firm attachment in the bone; and
   the curvature of the one or more shape cutting edges corresponds to the curvature of bone contact surface of the specific implant to be implanted.

6. The drill tool according to claim 3, wherein the size and shape of the specific implant to be implanted corresponds in large or partly or substantially to the size and shape of a cartilage damage in a specific patient.

7. The drill tool according to claim 3, wherein the one or more shape cutting edges in side view are designed to correspond to the shape of at least one side of a bone contacting surface in a cross-sectional view of the specific implant to be implanted, and wherein the bone contacting surface is substantially flat or a bone contacting surface which comprises a protruding anchoring ring portion.

8. The drill tool according to claim 7, wherein the one or more shape cutting edges are provided with at least one protruding flange corresponding to said protruding anchoring ring portion.

9. The drill tool according to claim 3, wherein an angle between the one or more shape cutting edges and the longitudinal y-axis is based on a corresponding angle of the specific implant to be implanted.

10. The drill tool according to claim 1, wherein the second diameter recess has a uniform cross-section perpendicular to the y-axis throughout the depth of the second diameter recess.

11. A kit comprising the drill tool according to claim 3 and the specific implant to be implanted.

12. An implant specific drill bit comprising:
a drill and bone remover body having a proximal end and a distal end and a longitudinal axis extending between the proximal end and the distal end;
a bone remover part located at the proximal end of the drill and bone remover body; and
a central drill part located at the distal end of the drill and bone remover body and protruding from the bone remover part;
wherein said bone remover part comprises one or more shape cutting edges facing the distal end along the longitudinal axis and placed peripherally around the central drill part, wherein said one or more shape cutting edges comprises one or more sharp pre-cutting edges extending 0.3 to 3 mm longitudinally towards the distal end from each of said one or more shape cutting edges without contacting the central drill part.

13. The implant specific drill bit according to claim 12, wherein the one or more shape cutting edges comprise a flat surface or a surface which further comprises flanges.

14. A kit comprising the implant specific drill bit according to claim 12 and a specific implant to be implanted.

* * * * *